(12) United States Patent
Ellis et al.

(10) Patent No.: US 8,235,627 B2
(45) Date of Patent: Aug. 7, 2012

(54) SYSTEM AND METHOD FOR DETECTING AND REMEDIATING CONTAMINATION

(76) Inventors: Mark T. Ellis, Lehi, UT (US); Son Q. Le, Orem, UT (US); Larry J. Davis, Woodland Hills, UT (US)

(*) Notice: Subject to any disclaimer, the term of this patent is extended or adjusted under 35 U.S.C. 154(b) by 1241 days.

(21) Appl. No.: 11/548,559

(22) Filed: Oct. 11, 2006

(65) Prior Publication Data

US 2007/0131864 A1 Jun. 14, 2007

Related U.S. Application Data

(63) Continuation-in-part of application No. 11/164,877, filed on Dec. 8, 2005.

(51) Int. Cl.
*E02B 13/00* (2006.01)
(52) U.S. Cl. .............. 405/52; 405/128.1; 405/128.15; 405/128.45; 405/128.7; 166/268; 210/170.07
(58) Field of Classification Search .... 405/128.1–128.9; 166/268, 401; 210/170.07
See application file for complete search history.

(56) References Cited

U.S. PATENT DOCUMENTS

| | | | | |
|---|---|---|---|---|
| 4,754,655 A * | 7/1988 | Parker et al. | ............ | 73/864.44 |
| 5,494,640 A | 2/1996 | Simon et al. | | |
| 6,147,351 A | 11/2000 | Huiku | | |
| 6,230,545 B1 | 5/2001 | Adolph et al. | | |
| 6,464,005 B1 * | 10/2002 | Ellis | ............ | 166/268 |
| 6,827,861 B2 * | 12/2004 | Kerfoot | ............ | 210/741 |
| 7,705,312 B2 | 4/2010 | Ellis et al. | | |
| 2004/0237505 A1 | 12/2004 | Leipertz | | |
| 2006/0256330 A1 | 11/2006 | Leipertz | | |

* cited by examiner

*Primary Examiner* — In Suk Bullock
*Assistant Examiner* — Robert Eom
(74) *Attorney, Agent, or Firm* — Kirton McConkie; N. Kenneth Burraston

(57) ABSTRACT

A system for detecting and remediating a discharge of fuel from a fuel source facility is disclosed. The system can comprise a contamination detection subsystem configured to detect a discharge of fuel from the fuel source facility and a remediation subsystem configured to remediate contamination due to the discharge of fuel. A controller can automatically activate the remediation subsystem upon detection of a discharge by the contamination detection subsystem. The controller can automatically send a notification that a contamination has been detected and the remediation system has been activated. Alternatively or in addition, the controller can automatically send a notification that a contamination has been detected and the remediation system has been activated.

21 Claims, 16 Drawing Sheets

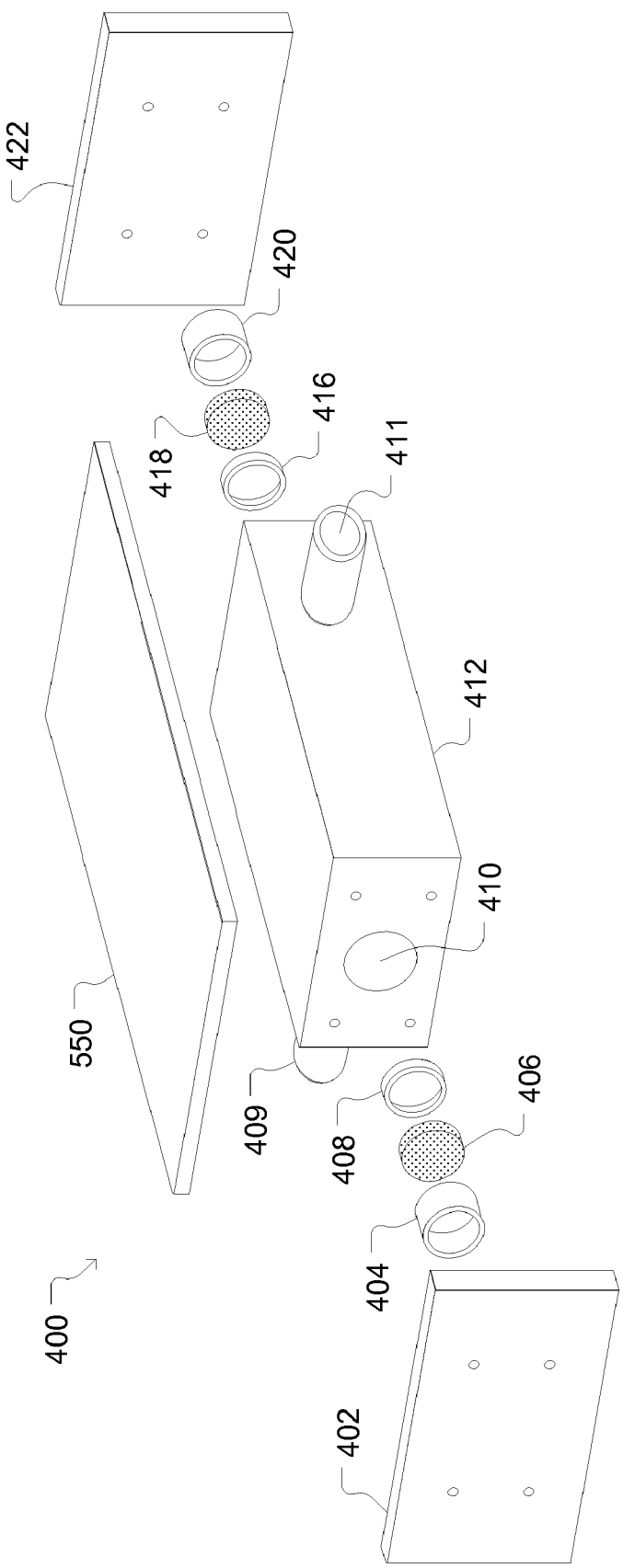

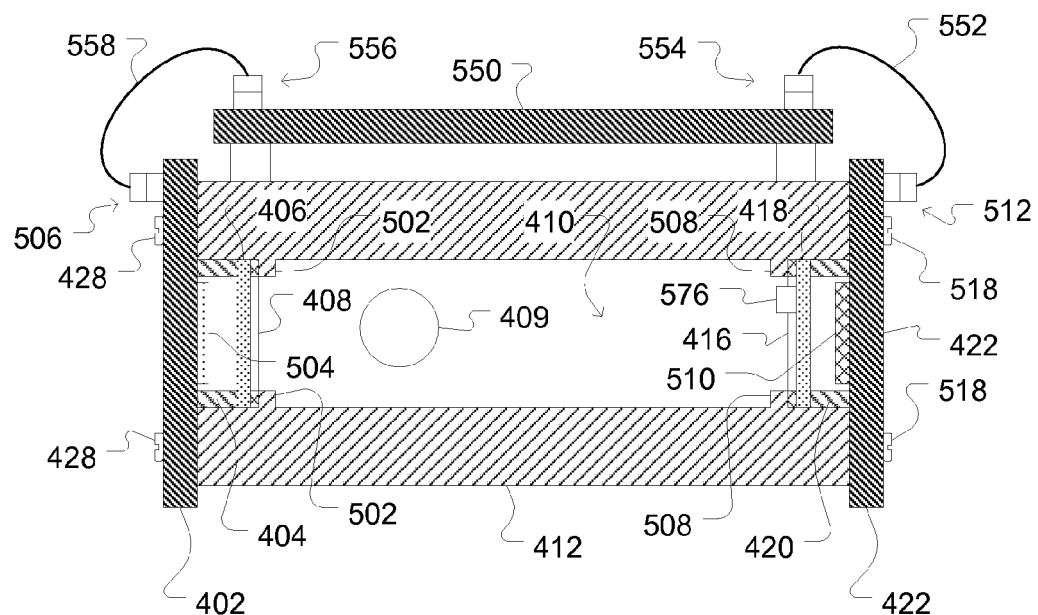
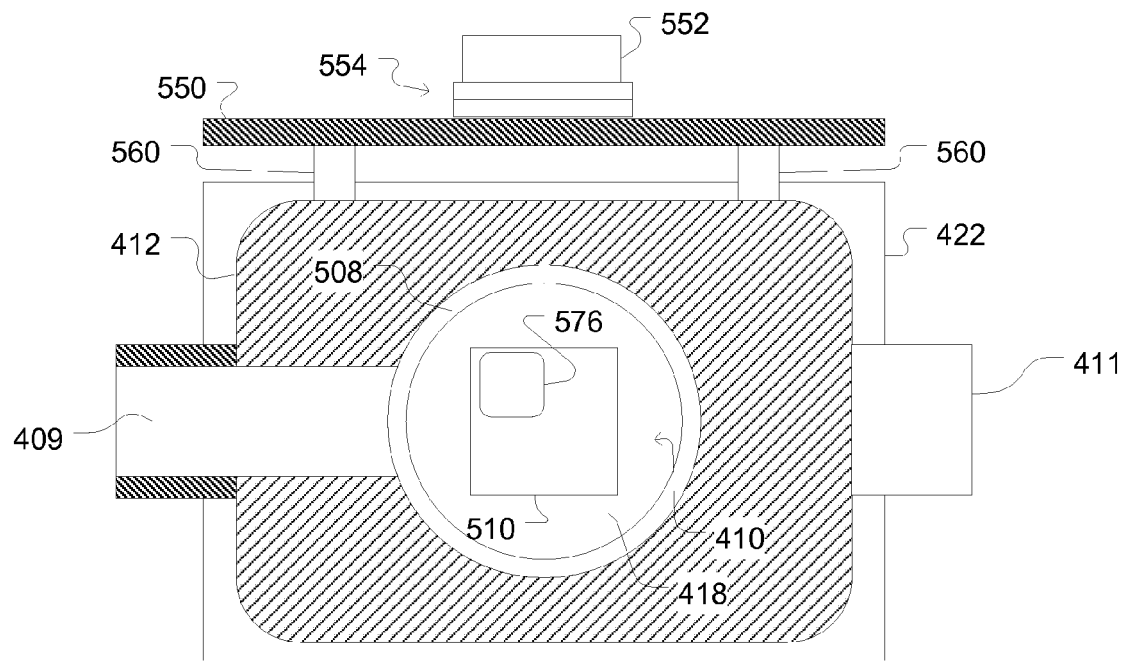

SYSTEM AND METHOD FOR DETECTING AND REMEDIATING CONTAMINATION

CROSS-REFERENCE TO RELATED APPLICATION(S)

This application is a continuation-in-part of U.S. patent application Ser. No. 11/164,877, filed Dec. 8, 2005.

BACKGROUND

In the modern industrial age, there are many facilities that make, store, or dispense materials that may be harmful to the environment if discharged. Examples of such facilities include without limitation fuel stations for dispensing fuel to automobiles, trucks, airplanes, locomotives, etc. (a neighborhood gasoline station is one example of such a fuel station); factories for making chemicals, plastics, steel, or any product in which the process of manufacture involves the use of a material that may be harmful to the environment; storage facilities for fuel, chemicals, or any potentially harmful or dangerous material. Improved methods and systems for detecting discharges from such facilities are needed.

SUMMARY

Some embodiments of the invention comprise a system for detecting and remediating a discharge of fuel from a fuel source facility. The system can comprise a contamination detection subsystem configured to detect a discharge of fuel from the fuel source facility and a remediation subsystem configured to remediate contamination due to the discharge of fuel. A controller can automatically activate the remediation subsystem upon detection of a discharge by the contamination detection subsystem.

DESCRIPTION OF THE DRAWINGS

FIG. 6 illustrates an exploded, perspective view of the gas sensor of FIG. 5A.

FIGS. 7 and 8 illustrate side, cross-sectional views of the sensor of FIG. 5A.

DETAILED DESCRIPTION OF EXEMPLARY EMBODIMENTS

This specification describes exemplary embodiments and applications of the invention. The invention, however, is not limited to these exemplary embodiments and applications or to the manner in which the exemplary embodiments and applications operate or are described herein.

Figure 1:
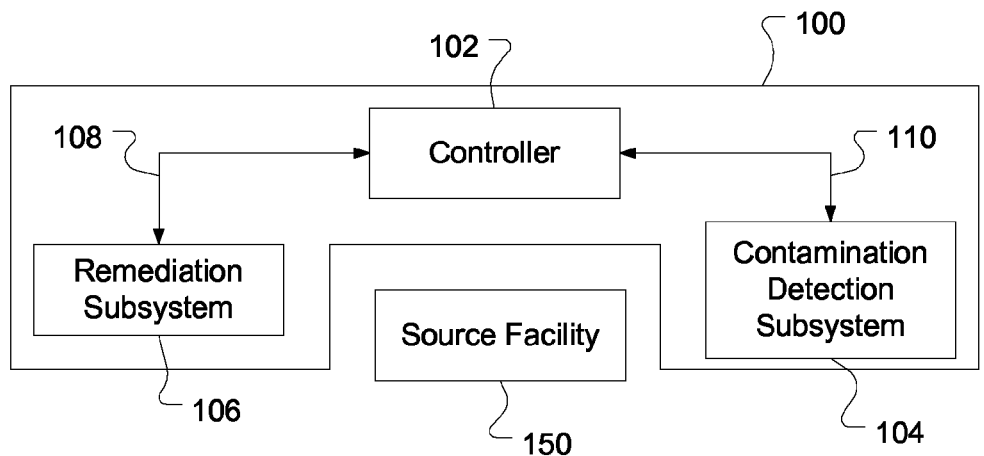
FIG. 1 illustrates an exemplary contamination detection and remediation system for detecting and remedying contamination by a source facility according to some embodiments of the invention.

FIG. 1 illustrates an exemplary system 100 for detecting and remediating contamination from source facility 150 according to some embodiments of the invention. Source facility 150 may be any system that can discharge contaminants (i.e., any potentially damaging, harmful, or otherwise unwanted substance or substances) into the surrounding environment. (As used herein, the term "discharge" refers to any unwanted, unintended, or potentially harmful discharge, leak, drainage, or escape from or within source facility 150.) Non-limiting examples of such a source facility 150 include fuel dispensing facilities, such as fuel stations for dispensing gasoline and diesel to automobiles and trucks. Non-limiting examples of other fuel dispensing facilities include stations for dispensing fuel to airplanes, boats, railroad locomotives, or any other device that utilizes fuel. Other non-limiting examples of a source facility 150 include factories (e.g., petroleum refineries, chemical factories, fertilizer factories, steel refineries, plastics factories, computer factories, automobile factories, or any factory that utilizes potentially harmful, damaging, or unwanted materials that may discharge. A still further non-limiting example of a source facility is a storage facility including without limitation a facility for storing fuel, chemicals, or any other substance that may be harmful to the environment if discharged. Another example of a source facility is a construction site. Indeed, source facility 150 may be any facility or site at which materials that may be harmful, damaging, or unwanted if discharged are used, made, stored, dispensed, sold, etc.

As shown in FIG. 1, the detection and remediation system 100 includes a controller 102, a contamination detection subsystem 104, and a remediation subsystem 106.

Contamination detection subsystem 104 is configured to detect a discharge of one or more contaminants from source facility 150. The make up and configuration of contamination detection subsystem 104 depends on the source facility 150. Contamination detection subsystem 104 is configured to detect the type or types of contaminants that source facility 150 may discharge. For example, if source facility 150 is a storage facility for aviation fuel, contamination detection system 104 may be configured to detect jet fuel and/or chemical elements of jet fuel in the soil and/or ground water in and around the storage facility. A non-limiting specific example of contamination detection subsystem 104 in which the source facility 150 is a gasoline and/or diesel dispensing station will be discussed in detail below.

Remediation subsystem 106 is configured to remediate a discharge of contaminants from source facility 150. Like contamination detection subsystem 104, the make up and configuration of remediation subsystem 106 depends on the source facility 150. That is, remediation subsystem 106 is configured to remediate the type or types of contaminants that source facility 150 may discharge. Continuing with the above example in which source facility 150 is a storage facility for aviation fuel, remediation subsystem 106 may be configured to remediate jet fuel and/or chemical elements of jet fuel discharged into the soil and/or ground water in and around the storage facility. A non-limiting specific example of remediation system 106 in which the source facility 150 is a gasoline and/or diesel dispensing station will be discussed in detail below.

Controller 102 controls overall operation of the detection and remediation system 100 (but not necessarily source facility 150), and communications connections 108 and 110 communicatively connect controller 102 with contamination detection system 104 and remediation subsystem 106 as shown in FIG. 1. Each of communications connections 106, 108 may be any type of data link including, without limitation, a digital data bus (parallel or serial), a coaxial cable, a twisted pair of conductive wires, a radio frequency or infrared wireless link, etc. In operation, controller 102 receives data via communications connection 110 from contamination detection subsystem 104 and determines whether one or more contaminants have discharged from source facility 150. Controller 102 may also attempt to identify the specific contaminant or contaminants discharged from source facility 150, the locations of the discharge in or around source facility 150, and/or the amount or approximate amount of the contaminants discharged. Controller 102 then communicates via communications connection 108 control data to remediation system 106, activating remediation system 106 to remediate the detected discharge. Controller 102 may also receive general operating status data and control general operation of contamination detection subsystem 104 and remediation subsystem 106 via communications connections 108, 110.

Controller 102 may be any electronic or electromechanical system suitable for controlling operation of detection and remediation system 100. For example, controller 102 may comprise a digital computer or computer system in which functions performed by controller 102 are configured in software (e.g., software, microcode, firmware, etc.). Alternatively, the functions performed by controller 102 may be configured in hardwired logic circuits or in a combination of software and hardwire logic circuits.

Figure 2:
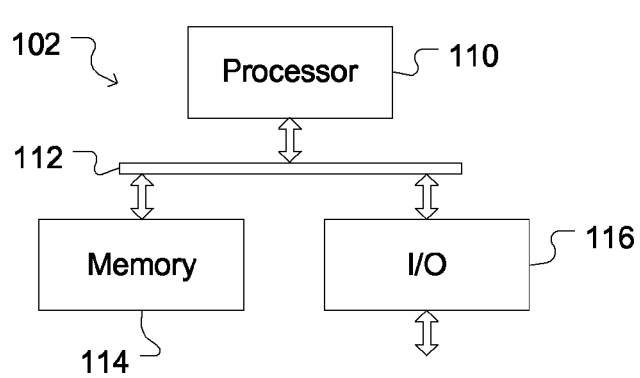
FIG. 2 illustrates an exemplary configuration of the controller of FIG. 1 according to some embodiments of the invention.

FIG. 2 illustrates one exemplary embodiment of controller 102 in which controller 102 comprises a digital processor 110, digital data bus 112, digital memory 114, and input/output (I/O) module 116. Digital processor 110 may be a microprocessor, microcontroller, or other digital processor configured to operate in accordance with software stored in memory 114, which may be any type of digital storage device including without limitation semiconductor, magnetic, or optical based digital memory devices. I/O module 116 provides for input and output of data into and out of controller 102. For example, I/O module 116 provides inputs and outputs for communications connections 108 and 110. Bus 112 provides communications among the processor 110, memory 114, and I/O module 116. Some or all of the functions performed by processor 110 may be hardwired in digital logic circuits rather than programmed in software.

Figure 3:
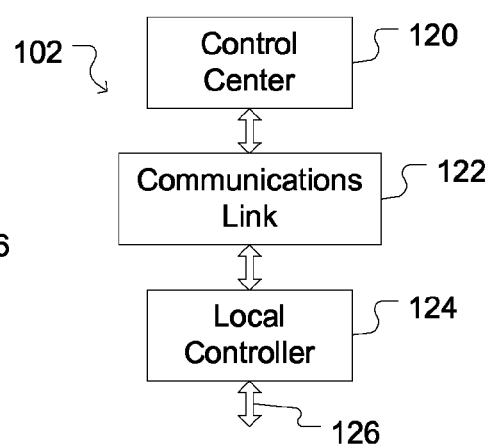
FIG. 3 illustrates another exemplary embodiment of the controller of FIG. 1 according to some embodiments of the invention.

FIG. 3 illustrates another exemplary embodiment of controller 102. As shown in FIG. 3, in this embodiment, controller 102 comprises a local controller 124, a communications link 122, and a control center 120. Local controller 124 is located generally near source facility 150, contamination detection subsystem 104, and remediation subsystem 106. Input and output ports 126 of local controller 124 are connected to communications connections 108, 110. Control center 120, on the other hand, may be remotely located from the source facility 150, contamination detection subsystem 104, and remediation subsystem 106. For example, control center 120 may be located many miles from source facility 150. Indeed, control center 120 may be located in a different, county, state, or country, or even on a different continent than source facility 150.

Local controller 124 may comprise a computer or a computer system operating under software control. As another example, local controller 124 may comprise a processor, bus, memory, and I/O module configured as shown in FIG. 2. Some or all of the functions performed by local controller 124 may be programmed into software, hardwired in digital logic circuits, or provided in a combination of software and hardwired circuitry. Control center 120 may likewise comprise one or more computers or computer systems, including a configuration like that shown in FIG. 2, and/or be configured to operate under software, hardware, or software and hardware control.

Communications link 122 provides communication between local controller 124 and control center 120. Communications link 122 may be any means of communications suitable for communicatively connecting local controller 124 and control center 120. For example, communications link 122 may comprise one or more distributed computer networks to which the local controller 124 and control center 120 are connected. As just one example, such a computer network may include the public Internet. As another example, communications link 122 may comprise a telephone system, including without limitation one or more land based telephone systems and/or one or more cellular telephone systems. As yet another example, communications link 122 may include one or more radio frequency or other wireless communications devices. Communications link 122 may include the use of satellite communications devices. As still another example, communications link 122 may include one or more communications cables (e.g., coaxial cables) connecting local controller 124 with control center 120. Of course, communications link 122 may comprise more than one of the foregoing types of communications devices or systems. For example, communications link 122 may comprise two computer networks linked by a satellite communications system.

Figure 4:
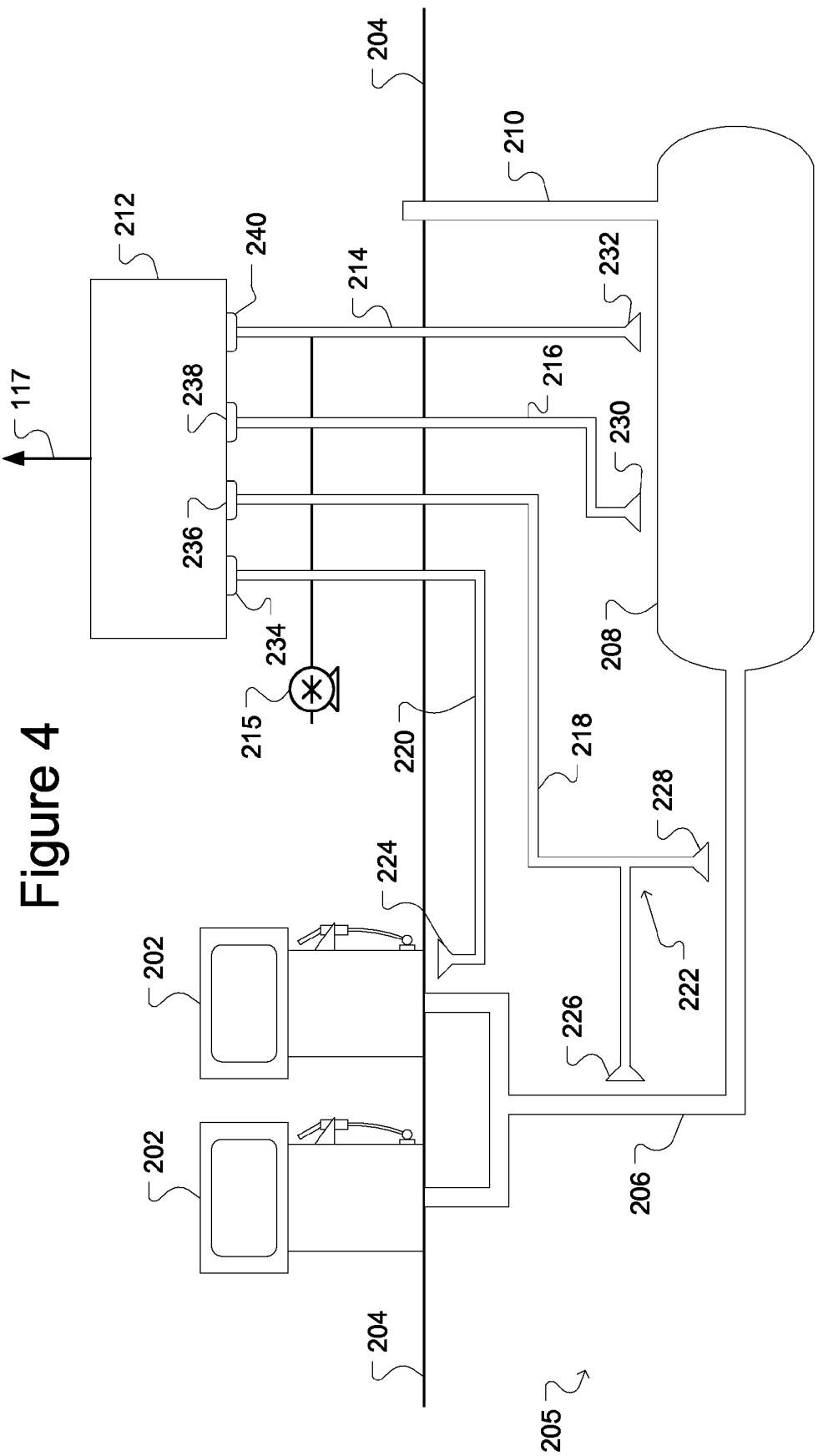
FIG. 4 illustrates a side view of an exemplary configuration of the contamination detection subsystem of FIG. 1 deployed with an exemplary source facility according to some embodiments of the invention.

FIG. 4 illustrates an exemplary embodiment of contamination detection subsystem 104 configured for use with a source facility 150 that is a fueling station providing sale of gasoline and/or diesel fuels to operators of automobiles and trucks. In FIG. 4, line 204 represents ground surface, and the area below ground line 204 represents ground soil and/or ground water 205. The fueling station shown in FIG. 4 includes an underground fuel storage tank 208 and pumps 202 for pumping fuel from the storage tank 208 through pipe system 206 and a pump 202 into an automobile or truck (not shown). The storage tank 208 may be supplied with fuel through fill line 210.

The contamination detection subsystem shown in FIG. 4 includes a plurality of intake lines 214, 216, 218, 220, and a gas sensor 212. Each intake line 214, 216, 218, 220 includes at least one inlet port 224, 226, 228, 230, 232, which may include a screen, and each intake line is connected to an input tap 234, 236, 238, 240 of sensor 212. As shown, intake line 214 includes inlet port 232 at one end, and the other end of intake line 214 is connected to input tap 240 of sensor 212. Intake line 216 likewise includes inlet port 230 at one end, and the other end of intake line 214 is connected to input tap 238 of sensor 212. As also shown in FIG. 4, intake line 218 includes two inlet ports 226 and 228 and is connected to input tap 236 of sensor 212 (intake line 218 includes branch 222), and intake line 220 includes inlet port 224 and is connected to input tap 234 of sensor 212. The system of input ports 224, 226, 228, 230, 232 and intake lines 214, 216, 218, 222 can alternatively be replaced by a manifolded gas distribution array, which can be disposed to provide gas or vapor samples from various locations in the ground soil 205 to the sensor 212.

Inlet ports 224, 226, 228, 230, 232 include perforations that allow for the passage of air and other gases from the ground soil 205 into intake lines 214, 216, 218, 220. The perforations in inlet ports 224, 226, 228, 230, 232 may be as simple as holes in intake lines 214, 216, 218, 220 or may include additional hardware, such as a wire screen, a mesh structure, or a filter.

Intake lines 214, 216, 218, 220 may be pipes, such as earthen pipes or non-earthen synthetic pipes (e.g., PVC or metal pipes). As shown in FIG. 4, one or more air pumps 215 are connected to the intake lines 214, 216, 218, 220. While air pump 215 is operating, air and other gases are drawn out of the ground soil 205 into inlet ports 224, 226, 228, 230, 232, through intake lines 214, 216, 218, 220 and into input taps 234, 236, 238, 240 of sensor 212.

Sensor 212 is configured to detect contaminants that would be introduced into or produced in ground soil 205 due to a discharge in storage tank 208, pipe system 206, or pumps 202. In the example shown in FIG. 4, storage tank 208, pipe system 206, or pumps 202 are configured to dispense gasoline or other types of fuel. A discharge of gasoline or other fuels into ground soil 205 is likely to cause particular gases or vapors to be present in the ground soil 205. Thus, sensor 212 may be configured to detect particular concentrations of the gas, gases, vapor, or vapors likely to be in ground soil 205 due to a discharge of fuel from the source facility comprising pumps 202, pipe system 206, storage tank 208, and fill line 210 or due to surface spills that percolate into the ground soil 205 (which as mentioned above can also include ground water). Although only one storage tank 208 and pipe system 206 is shown in FIG. 4, additional storage tanks 208 and pipe systems 206 may be present and may store and dispense a variety of different fuels (e.g., gasoline, diesel, etc.). For example, the source facility shown in FIG. 4 (comprising pumps 202, pipe system 206, storage 208, and fill line 210) may be configured to store and dispense gasoline and diesel fuels for distribution to automobiles and trucks. In such a case, sensor 212 may also be configured to sense the presence of gasoline vapors and/or diesel vapors in the air and gases drawn into the sensor 212 from ground soil 205 through inlet ports 224, 226, 228, 230, 232 and intake lines 214, 216, 218, 220. A discharge of diesel fuels (e.g., for certain types of automobiles and for many types of trucks) is likely to cause increased concentrations of hydrocarbons (e.g., $C_{12[1]}$-$C_{35}$ hydrocarbons, methane ($CH_4$), etc.) in ground soil 205. Sensor 212 may thus be configured to detect hydrocarbons (e.g., $C_{12[1]}$-$C_{35}$ hydrocarbons, methane ($CH_4$), etc.) in the air, vapors, and gases drawn from ground soil 205 through inlet ports 224, 226, 228, 230, 232. Indeed, the sensor 212 can be configured to detect a wide range of hydrocarbons (e.g., $C_1$-$C_{35+}$). As will be discussed below, concentrations of hydrocarbons and/or other gases (e.g., oxygen, carbon dioxide, etc.) can be monitored during remediation of a discharge by remediation subsystem 106, and sensor 212 can thus also be configured to detect concentrations of gases (e.g., oxygen, carbon dioxide, etc.) that indicate remediation progress.

Many configurations and implementations of such sensors are known and can be used for sensor 212. For example, such sensors can comprise filters that absorb specific gases or vapors and mechanisms that produce a detectable reaction in the presence of those gases or vapors. One non-limiting example of a suitable sensor that can be used for sensor 212 is disclosed in U.S. patent application Ser. No. 11/164,877 filed Dec. 8, 2005 and entitled Multi-Gas Sensor. The foregoing application (bearing Ser. No. 11/164,877) is incorporated herein in its entirety by reference, and FIGS. 1A-7 of that patent application are reproduced herein as FIGS. 5A-11 and discussed below.

FIGS. 5A-11 illustrate an exemplary multi-gas sensor 400 according to some embodiments of the invention. Sensor 400 is a multi-gas sensor that can be configured to detect a plurality of gases including vapors (e.g., hydrocarbon based vapors, carbon dioxide, oxygen, acid vapors, chlorinated solvents, ammonia, methanol, isopropyl alcohol, ether, etc.). As shown in FIGS. 5A-11, the sensor 400 includes a body 412 that comprises a gas chamber 410 (best seen in FIG. 7). An inlet port 411 allows gas that is to be tested to enter the chamber 410, and an outlet port 409 allows the gas to exit the chamber 410. The body 412 may be formed of any durable material such as steel, inert plastic, etc. The body 412 may be constructed of a material that does not react substantially with the gases that will be introduced into the chamber 410. Alternatively or in addition, surfaces of the inlet port 411, outlet port 409, and chamber 410 may be coated with a material that does not react substantially with the gases that will be introduced into the chamber 410 or otherwise treated to reduce reactions with those gases. For example, chamber 410 may be coated in whole or in part with one or more thermoplastic resins. As one non-limiting example, thermoplastic resins marketed by General Electric Company under the trade name Valox® can be used.

As shown in FIGS. 5A-11, sensor 400 may include one or more circuit boards to which electronic components are attached to form an electronic circuit for controlling and operating the sensor 400. In the example shown in FIGS. 5A-11, sensor 400 includes three circuit boards 402, 422, and 550, although fewer or more circuit boards may be used in other implementations of sensor 400. In the example shown in FIGS. 5A-8, fasteners 428 (e.g., screws or bolts) attach first circuit board 402 to body 412, and fasteners 518 (e.g., screws or bolts) attach second circuit board 422 to the opposite end of body 412. Third circuit board 550 may also be attached to body 412 using screws, bolts, or other fasteners (not shown), and as shown in FIGS. 6-8, spacers 560 may be disposed between third circuit board 550 and body 412.

Electrical components (not shown), such as one or more resistors, capacitors, inductors, integrated circuits, processors, memories, etc. may be disposed on the circuit boards 402, 422, 550 and electrically connected to form one or more circuits (not shown) for controlling and implementing operation of sensor 400. As shown in FIGS. 5A-8, electrical connectors 506, 556, 558 may provide electrical connections between first circuit board 402 and third circuit board 550, and electrical connectors 512, 552, 554 may provide electrical connections between second circuit board 422 and third circuit board 550. Connectors 506 and 556 may be, for example, zero insertion force ("ZIF") connectors, and connector 558 may be a ribbon cable. Connectors 512, 552 may likewise be ZIP connectors, and connector 552 may be a ribbon cable.

As shown in FIG. 7, the circuitry disposed on first circuit board 402 may include an energy source element 504, and the circuitry disposed on second circuit board 422 may include detector element 510. The energy source element 504 may be configured to direct one or more beams of energy through chamber 410 and onto detector element 510, which detects the amount of energy in the beam or beams. Electronics (not shown) disposed on one or more of circuit boards 402, 422, 550 may be configured to control the generation of energy beams by energy source element 504 and the detection of those energy beams at detection element 510. That electronics (not shown) may also be configured to determine, for each such energy beam, a difference in the energy of the beam as generated by the energy source element 504 and the energy of the beam as detected at the detector element 510. This difference in energy is due primarily to absorption of energy from the beam by one or more gases in chamber 410. Thus, as will be discussed in more detail below, the presence and even the concentration of certain gases in the chamber 410 can be determined based on the loss in energy of particular energy beams as those beams pass through chamber 410. Provisions may also be made to detect one or more gases in chamber 410 that do not absorb energy from beams generated by energy source element 504.

In FIG. 7, an exemplary special detector element 576 is located within chamber 410 and configured to detect the presence and/or an approximate concentration of a particular gas in chamber 410. The particular configuration of special detector element 576 will depend on the gas the special detector element 576 is to detect. For example, special detector element 576 may be impregnated with a material that reacts in a known and detectable manner to the presence of a particular gas in chamber 410.

As best seen in FIG. 7, a first isolation window assembly comprising a first sealant ring 408, a first isolation window 406, and a first locating element 404 is disposed within body 412 to isolate first circuit board 402 and energy source element 504 from gases in chamber 410. As shown in FIG. 7, while first circuit board 402 is fastened to body 412, first locating element 404 presses first isolation window 406 and sealing ring 408 against a first rim 502 in chamber 410. First isolation window 406 is thus held securely in place, and sealing ring 408 prevents appreciable levels of gas from escaping from chamber 410.

First sealing ring 408 may be any suitable element sufficient to prevent appreciable levels of gas from escaping from chamber 410. For example, first sealing ring 408 may be a rubber O-ring. First isolation window 406 may be any suitable element configured to allow energy beams generated by energy source element 504 to pass. First isolation window 406 may comprise a material or materials that do not react appreciably with the types of gases that are expected to be introduced into chamber 410. As one non-limiting example, first isolation window 406 may be a sapphire window. First locating element 404 may be a bushing or other mechanical element sized to press first isolation window 406 and first sealing ring 408 against first rim 502 with sufficient force to create an adequate seal against appreciable escape of gas around first isolation window 406 from chamber 410 but not to break or damage first isolation window 406.

A similar second isolation window assembly comprising a second sealant ring 416, a second isolation window 418, and a second locating element 420 is also disposed within body 412 to isolate second circuit board 422 and detector element 510 from gases in chamber 410. The second isolation window assembly is pressed against a second rim 508 in chamber 410 and may be constructed like and made of the same or similar materials as the first isolation window assembly as discussed above.

The first and second isolation window assemblies protect first circuit board 402, including energy source element 504, and second circuit board 422, including detector element 510, from gases in chamber 410, at least some of which may be corrosive. Thus, only special detector element 576 is directly exposed to the gases in chamber 410.

Figure 9:
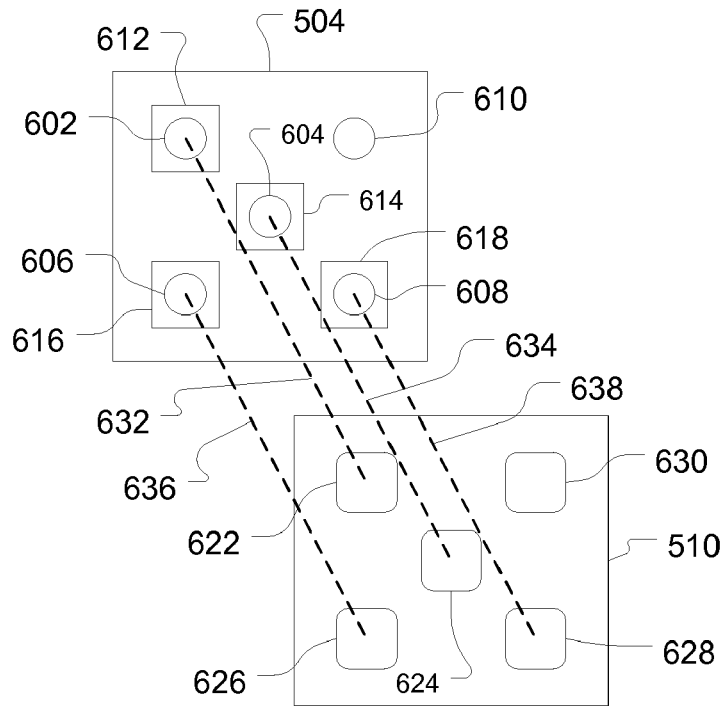
FIG. 9 illustrates a perspective view of an exemplary configuration of the energy source element and the detector element of the sensor of FIG. 5A according to some embodiments of the invention.
Figure 10:
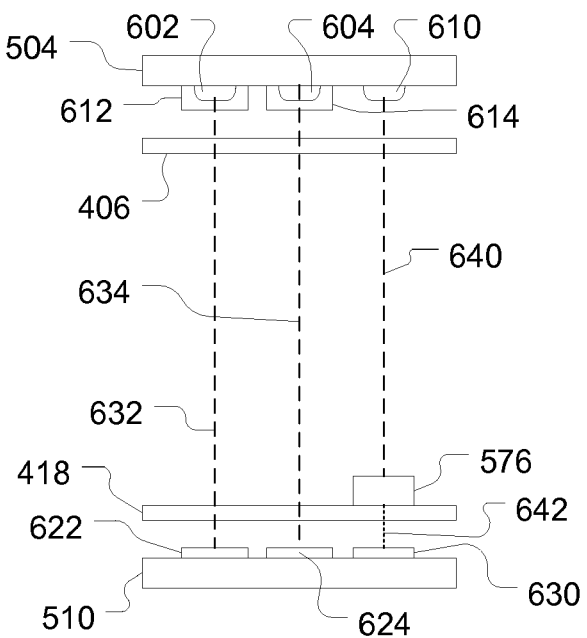
FIG. 10 illustrates a top view of the illustration shown in FIG. 9 further including first isolation window and second isolation window with special detector element.

FIGS. 9 and 10 illustrate an exemplary, non-limiting configuration of energy source element 504 and detector element 510 in which those elements are configured to detect the presence of carbon dioxide ($CO_2$), hydrocarbons (e.g., $C_{12[1]}$-$C_{35}$ hydrocarbons, methane ($CH_4$), etc.), and oxygen ($O_2$) in chamber 410 of sensor 400 and, if present, determine concentrations of those gases. Of course, in other embodiments, energy source element 504 and detector element 510 can be configured to detect other gases and/or vapors (e.g., carbon monoxide (CO)). FIG. 9 illustrates a perspective view of only energy source element 504 and detector element 510 as they are disposed in the assembled sensor 400 shown in FIG. 7. FIG. 10 illustrates a top view of the configuration shown in FIG. 9 and further shows isolation windows 406, 418 and special detector element 576.

Referring to FIG. 9, energy source 504 includes infrared (IR) beam sources 602, 604, 606, 608, each configured to generate a beam of IR energy having a particular energy level. The generation of the IR beams may be controlled by electronics (not shown) located on the one or more of circuit boards 402, 422, 550. Optical filters 612, 614, 616, 618 may be fitted over each IR source 602, 604, 606, 608. Each optical filter 612, 614, 616, 618 is configured to pass only IR energy that falls within a specified wavelength range. As shown in FIG. 9, first IR source 602 generates first IR beam 632, second IR source 604 generates second IR beam 634, third IR source 606 generates third IR beam 636, and fourth IR source 608 generates fourth IR beam 638.

Detector element 510 includes four energy sensors 622, 624, 626, 628 configured to sense an amount of energy in an IR beam that strikes the sensor. As shown in FIG. 9, first sensor 622 is positioned to be struck by first IR beam 632 generated by first IR source 602, second sensor 624 is positioned to be struck by second IR beam 634 generated by second IR source 604, third sensor 626 is positioned to be struck by third IR beam 636, and fourth sensor 628 is positioned to be struck by fourth IR beam 638 generated by fourth IR source 608. Although four sets of IR source, filter, and sensor are shown in FIG. 9, more or fewer may be used in a given implementation of sensor 400.

In the example shown in FIG. 9, three sets of IR source, filter, and sensor are configured to detect the presence and concentrations of three gases in chamber 410: certain hydrocarbons (e.g., $C_{12}$-$C_{35+}$), methane ($CH_4$), and carbon dioxide ($CO_2$). The other set of IR source, filter, and sensor is configured to act as a reference.

As is known, methane absorbs IR energy having a wavelength of about 3.3 microns or about 1.3 microns, carbon dioxide absorbs IR energy having a wavelength of about 4.27 microns, and hydrocarbons that include $C_{12}$-$C_{35+}$ absorb IR energy having a wavelength of about 3.4 microns. In the example shown in FIG. 5, first optical filter 612 is configured to pass IR energy having a wavelength of about 3.3 microns or about 1.3 microns (or wavelengths in a range that includes 3.3 microns or 1.3 microns), third optical filter 616 is configured to pass IR energy having a wavelength of about 4.27 microns (or wavelengths in a range that includes 4.27 microns), and fourth filter 618 is configured to pass IR energy having a wavelength of about 3.4 microns (or wavelengths in a range that includes 3.4 microns). First IR beam 632 thus consists of IR energy having a wavelength of about 3.3 microns (or wavelengths in a range that includes 3.3 microns), which will be absorbed by any methane gas in chamber 410; third IR beam 634 consists of IR energy having a wavelength of about 4.27 microns (or wavelengths in a range that includes 4.27 microns), which will be absorbed by any carbon dioxide gas in chamber 410; and fourth IR beam 638 consists of IR energy having a wavelength of about 3.4 microns (or wavelengths in a range that includes 3.4 microns), which will be absorbed by any hydrocarbons that include $C_{12[1]}$-$C_{35+}$ hydrocarbons in chamber 410. Second IR beam 634 will be used as a reference and is selected to have a wavelength that is not absorbed by carbon monoxide, carbon dioxide, or hydrocarbons in chamber 410. Thus, second filter 614 may be configured to pass any wavelength of IR energy generated by IR source 604 that is not absorbed by methane, carbon dioxide, or hydrocarbons having $C_1$-$C_{35+}$ with a vapor pressure. As one non-limiting example, filter 614 may be configured to pass a wavelength of 3.95 microns (or a range of wavelengths around 3.95 microns).

As will be discussed below with regard to the exemplary circuit configuration shown in FIG. 11, electronics (not shown) on one or more of the circuit boards 402, 422, 550 causes IR sources 602, 604, 606, 608 in conjunction with filters 612, 614, 616, 198 to generate IR beams 632, 634, 636, 638, which pass through the gases in chamber 410 (see FIGS. 7 and 8) and strike, respectively, IR sensors 622, 624, 626, 628, each of which outputs a signal indicative of the energy in one of beams 632, 634, 636, 638. As discussed above, second IR beam 634 is not absorbed by any of the gases expected to be in chamber 410, but methane in chamber 410 absorbs first IR beam 632, carbon dioxide in chamber 410 absorbs third IR beam 636, and hydrocarbons (e.g., $C_{12[1]}$-$C_{35+}$) in chamber 410 absorb fourth IR beam 638. Thus, if methane is present in chamber 410, the energy level of first IR beam 632 detected at first detector 622 will be less than the energy level of second IR beam 634 detected at second detector 624, and the difference in the energy level of first IR beam 632 and second IR beam 634 will be proportional to the concentration of methane in chamber 410. The presence and concentration of carbon dioxide in chamber 410 will similarly be indicated by a difference in the energy level of third IR beam 636 and second IR beam 634 at third and second detectors 624, 626, and the presence and concentrations of hydrocarbons (e.g., $C_{12[1]}$-$C_{35+}$) in chamber 410 will be indicated by a difference in the energy level of fourth IR beam 638 and second IR beam 634 at fourth and second detectors 624, 628. The electronics (not shown) on circuit boards 402, 422, 550 of sensor 400 may thus output signals that indicate the presence and approximate concentrations of methane, carbon dioxide, and hydrocarbons (e.g., $C_{12[1]}$-$C_{35+}$) in a gas sample introduced into chamber 410 of sensor 400.

Although the example shown in FIG. 9 is configured to detect the presence and concentrations of methane, carbon dioxide, and hydrocarbons (e.g., $C_{12[1]}$-$C_{35+}$), sensor 400 could alternatively be configured to detect the presence and concentrations of other gases. Indeed, any gas that is known to absorb energy may be detected by providing an energy source (e.g., like any of IR sources 602, 604, 606, 608) that directs a beam of energy known to be absorbed by the gas through chamber 410 of sensor 400 and against an energy sensor configured to detect an amount of energy in the beam after the beam passes through chamber 410. An appreciable loss of energy in the beam as it passes through chamber 410 of sensor 400 indicates the presence of the gas in chamber 410, and assuming proper calibration, the amount of energy loss is indicative of the concentration of the gas in the chamber 410 of sensor 400. Sensor 400 is thus not limited to detecting methane, carbon dioxide, or hydrocarbons (e.g., $C_{12[1]}$-$C_{35+}$) gases.

As mentioned above, some gases do not absorb IR or other forms of energy that are readily generated and passed through chamber 410 of sensor 400 in the form of a beam. Such gasses may nevertheless be detected by providing additional detection means within chamber 410. As shown in FIG. 10, special detector element 576 provides a non-limiting example for detecting oxygen in chamber 410. As is known, oxygen does not absorb IR energy.

Referring to FIG. 10, special detector element 576 is impregnated with a chemical that reacts with oxygen. Energy source 610 on energy source element 504 generates a beam of energy 640 that strikes special detector element 576, which excites the reactive chemical in special detector element 576. If oxygen is present around the special detector element 576 while the chemical reactant is excited, the chemical in special detector element 576 reacts with the oxygen and fluoresces. Such chemicals are known to those of ordinary skill in the field, and any such chemical can be used. A suitable chemical reactant can be obtained from PreSens—Precision Sensing GmbH located in BioPark Regensburg Germany (world-wide-web address www.presens.de). Sensor 630 on detector element 510 detects the fluorescent energy 642 generated by special detector element 576 and outputs a signal that is proportional to the amount of fluorescent energy detected. The amount of fluorescent energy generated by special detector element 576 is proportional to the concentration of oxygen around the special detector element 576, and thus, a signal output by sensor 630 is indicative of the presence and concentration of oxygen in chamber 410 of sensor 400. The electronics (not shown) on one or more of circuit boards 402, 422, 550 of sensor 400 may thus output a signal that indicates the presence and approximate concentration of oxygen in a gas sample introduced into chamber 410 of sensor 400.

Of course, sensor 400 may be configured to detect the presence of gases other than oxygen that do not absorb energy that can be passed through chamber 410. For example, any chemical or mechanism that reacts to a gas may be placed in chamber 410 and positioned to output energy indicative of the presence and/or concentration of the gas, and a detector may be positioned to detect the output energy and generate a signal indicative of the presence and/or concentration of the gas.

Figure 5A:
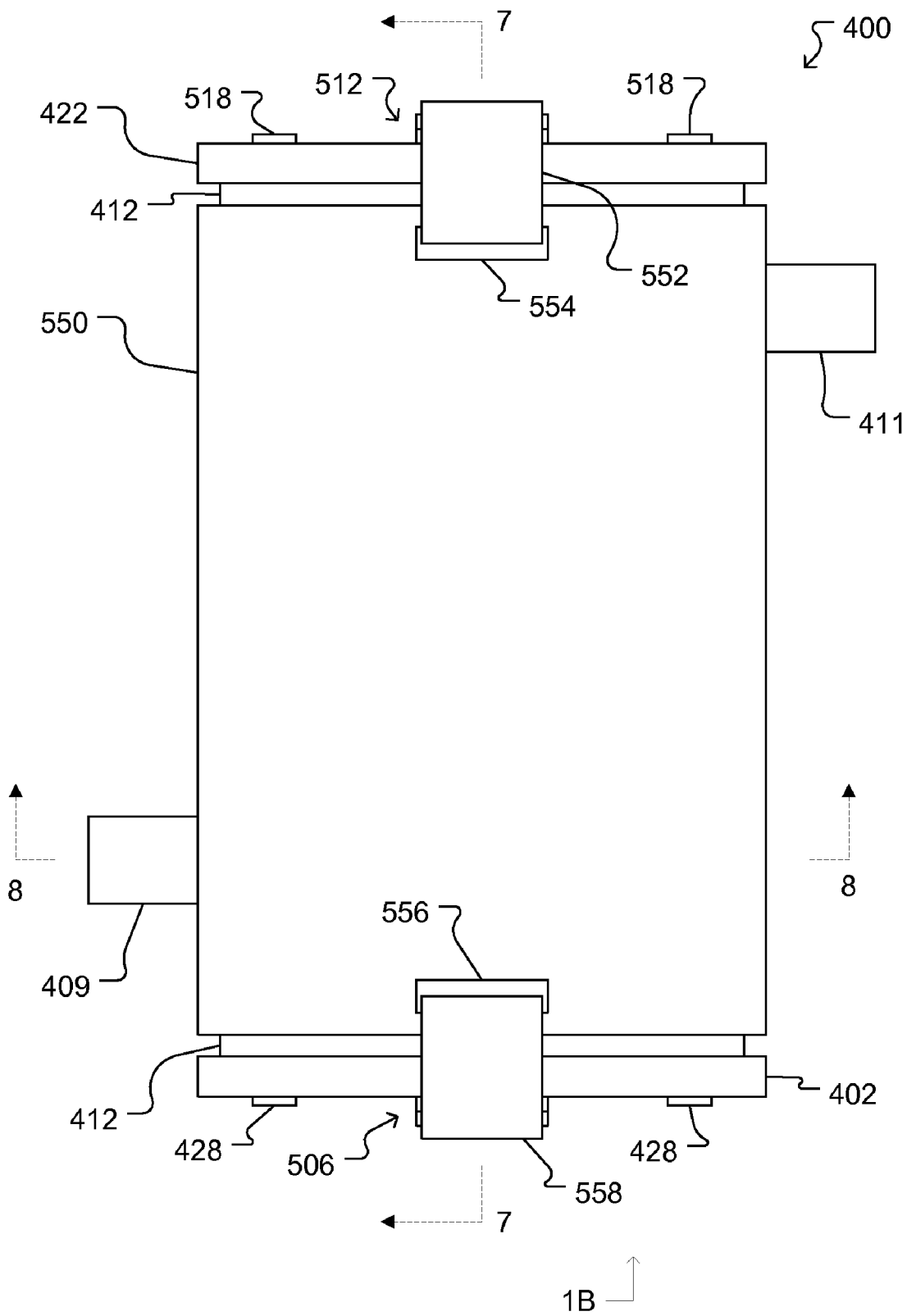
FIG. 5A illustrates a top view of an exemplary gas sensor according to some embodiments of the invention.
Figure 5B:
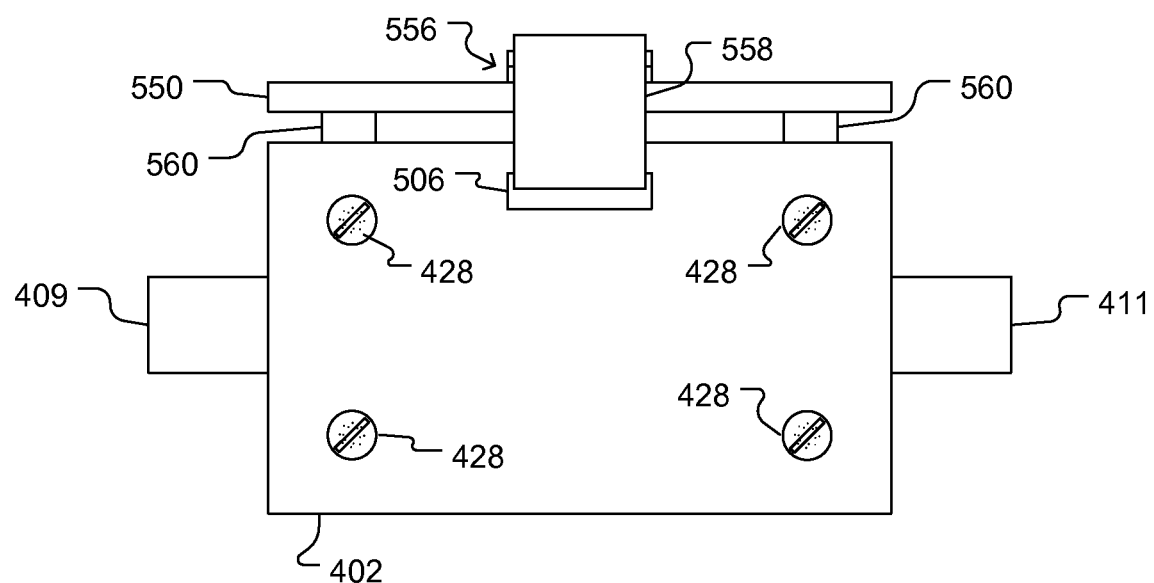
FIG. 5B illustrates a side view of the gas sensor of FIG. 5A.
Figure 11:
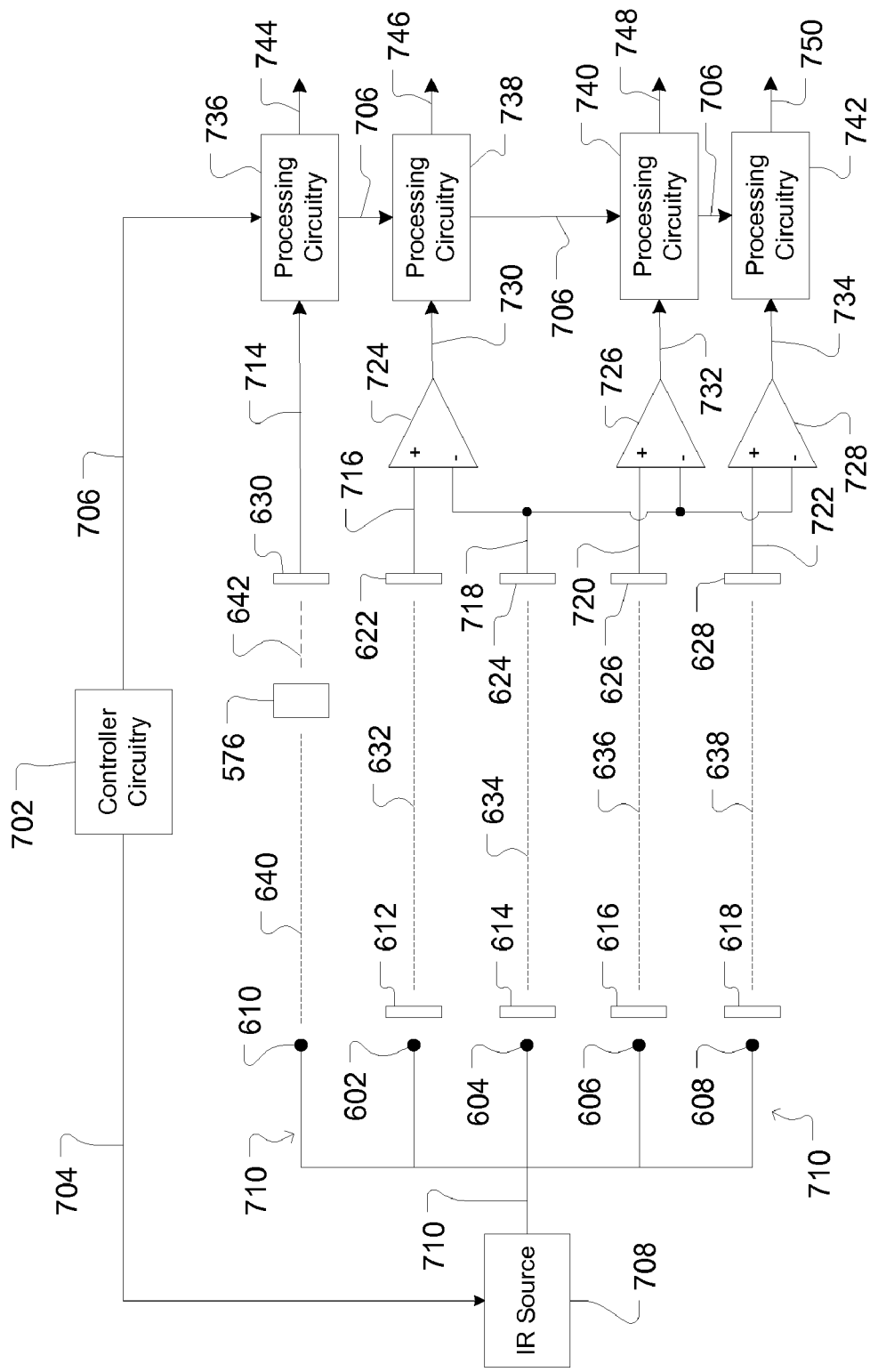
FIG. 11 illustrates an exemplary configuration of an electronic circuit for controlling and implementing operation of the sensor of FIG. 1A according to some embodiments of the invention.

FIG. 11 illustrates an exemplary configuration of circuitry for controlling and implementing operation of the energy source element 504, detector element 510, and special detector 576 of FIGS. 5 and 6. In the non-limiting exemplary configuration shown in FIG. 11, a IR source 708 generates IR energy, which is directed through branching fiber optics 710 the ends of which constitute energy sources 602, 604, 606, 608, 610 of FIG. 9. As discussed above, second beam 634 is a reference beam, and second sensor 624 outputs 718 a signal proportional to the energy level of second (reference) beam 634. As shown in FIG. 11, the output 718 of the second (reference) sensor 624 is input into one of the inputs of three differential amplifiers 724, 726, 728. As also shown in FIG. 11, the other input of each of differential amplifiers 724, 726, 728 is connected to the output of one of first sensor 622, third sensor 626, or fourth sensor 628. Differential amplifier 724 thus outputs 730 a signal proportional to the difference between the energy level of second (reference) beam 634 and first beam 632, which as described above is absorbed by carbon monoxide gas in chamber 410. The output 730 of differential amplifier 724 is thus indicative of the presence and concentration of methane gas in chamber 410. Differential amplifier 726 similarly outputs 732 a signal proportional to the difference between the energy level of second (reference) beam 634 and third beam 636, which as described above, is absorbed by carbon dioxide gas in chamber 410. The output 732 of differential amplifier 726 is thus indicative of the presence and concentration of carbon dioxide gas in chamber 410. In like manner, differential amplifier 728 similarly outputs 734 a signal proportional to the difference between the energy level of second (reference) beam 634 and fourth beam 638, which as described above, is absorbed by hydrocarbons (e.g., $C_1$-$C_{35+}$) in chamber 410. The output 734 of differential amplifier 728 is thus indicative of the presence and concentration of hydrocarbons (e.g., $C_1$-$C_{35+}$) in chamber 410. The output 714 of sensor 630 is an electrical signal that is proportional to the concentration of oxygen in chamber 410.

Processing circuitry 736, 738, 740, 742 processes each of output signals 714, 730, 732, 734. For example, processing circuitry 736, 738, 740, 742 may amplify signals 714, 730, 732, 734, convert those signals from analog form to digital form, and further convert the signals into a format suitable for display to a user of gas sensor 400. For example, the signals output 744, 746, 748, 750 by processing circuitry 736, 738, 740, 742 may be in a format suitable for display on any readout or display device. As another alternative, outputs 744, 746, 748, 750 may be stored in one or more electronic, magnetic, optical, or other storage devices. As still other alternatives, outputs 744, 746, 748, 750 may be transmitted to another device or entity. Of course, outputs 744, 746, 748, 750 may be further processed by electronics (not shown) at sensor 400. It should be apparent that output signal 744 indicates the presence of and/or concentration of oxygen in chamber 410, output signal 746 indicates the presence of and/or concentration of methane in chamber 410, output signal 748 indicates the presence of and/or concentration of carbon dioxide in chamber 410, and output signal 750 indicates the presence of and/or concentration of hydrocarbons (e.g., $C_1$-$C_{35+}$) in chamber 410.

As also shown in FIG. 11, control circuitry 702 controls IR source 708 and processing circuitry 736, 738, 740, 742 through control connections 704, 706. For example, control circuitry 702 may control the timing of generation of pulses of IR energy by IR source 708 and further control the processing of outputs 714, 730, 732, 734 by processing circuitry 736, 738, 740, 742. As one non-limiting example, control circuitry 702 may cause IR source 708 to generate a pulse of IR energy, which is directed through the chamber 410 as beams 640, 632, 634, 636, 638. Control circuitry 702 may then cause processing circuitry 736, 738, 740, 742 to latch and begin processing outputs 714, 730, 732, 734. Control circuitry 702 may cause IR source 708 to periodically produce such a pulse of IR energy and cause processing circuitry 736, 738, 740, 742 to periodically latch and process outputs 714, 730, 732, 734. Alternatively, control circuitry 702 may cause IR source 708 to generate a continuous beam of IR energy, and may cause processing circuitry 736, 738, 740, 742 to continuously or periodically process outputs 714, 724, 732, 734. Control circuitry 702 may comprise any combination of analog and/or digital circuitry including without limitation a microprocessor operating under control of software (including without limitation software, firmware, microcode, etc.).

Although the non-limiting exemplary configuration of sensor 400 shown in FIGS. 9-11 is configured to detect methane, carbon dioxide, hydrocarbons (e.g., $C_{12[1]}$-$C_{35+}$), and oxygen, as mentioned above, sensor 400 can be configured to detect other or additional gases and vapors, such as acid vapors, chlorinated solvents, ammonia, methanol, isopropyl alcohol, carbon monoxide, and ether. For each such gas or vapor that absorbs IR or other electromagnetic energy at a particular wavelength or in a particular wavelength range, energy source element 504 can be configured to generate an IR or other electromagnetic energy beam at the particular wavelength or within the particular wavelength range, and detector element 510 can be configured to determine an amount of energy lost as the beam passes through chamber 410, as generally described above with respect to FIGS. 9-11. For each such gas or vapor that does not absorb IR or other electromagnetic energy, a chemical reactant that reacts with the gas or vapor can be disposed within chamber 410 and detector element 510 can be configured to detect a chemical reaction with the chemical reactant as generally described above with respect to FIGS. 10 and 11.

Referring again to FIG. 4, sensor 212 can thus be configured to detect a wide variety of gases and vapors that may be found in gas samples extracted from ground soil 205 and introduced into sensor 212. Such gases and vapors include without limitation hydrocarbon based vapors (e.g., $C_{12[1]}$-$C_{35+}$ hydrocarbons, methane, etc.), carbon dioxide, carbon monoxide, oxygen, acid vapors, chlorinated solvents, ammonia, methanol, isopropyl alcohol, ether, etc.

As discussed above, the presence of appreciable concentrations of hydrocarbons (e.g., $C_1$-$C_{35+}$, methane, etc.) in the ground soil 205 (including ground water) around the gasoline fuel facility (storage tank 208, pipe system 206, and pumps 202) shown in FIG. 4 may be indicate a discharge. The sensor 400, configured as shown in FIGS. 5A-11, may thus be used as sensor 212 in FIG. 4 to detect appreciable concentrations of hydrocarbons (e.g., $C_1$-$C_{35+}$, methane, etc.). Air streams from intake lines 214, 216, 218, 220 are directed through inlet port 411 into chamber 410 of sensor 400 and IR energy sources 602, 606, 608 and light source 604 are activated. As discussed above, energy sensors 616, 620, 622 and light sensor 618 generate signals that are indicative of the presence and concentrations of hydrocarbons ($C_{12[1]}$-$C_{35+}$, methane, etc.) in the air streams from intake lines 214, 216, 218, 220. As also discussed above, concentrations of hydrocarbons ($C_{12[1]}$-$C_{35+}$, methane, etc.) greater than predetermined levels in the ground soil 205 (or the ground water) can indicate a discharge in the fuel dispensing system of FIG. 4 comprising storage tank 208, pipe system 206, and pumps 202.

Figure 12:
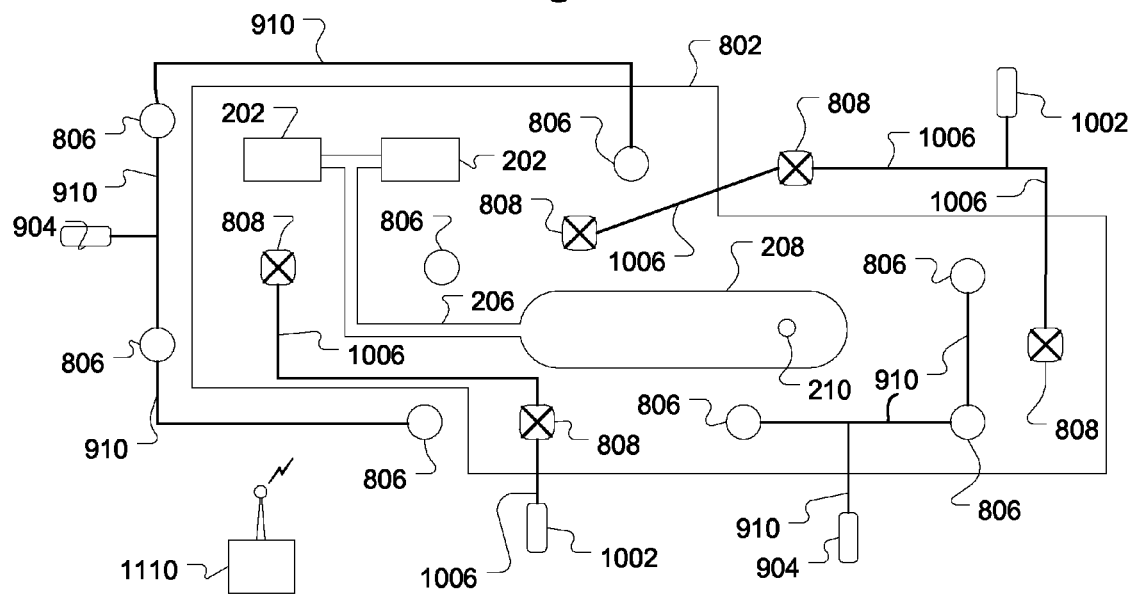
FIG. 12 illustrates a top view of an exemplary embodiment of the remediation subsystem of FIG. 1 deployed with the source facility and contamination detection subsystem of FIG. 4.

Referring again to the detection and remediation system of FIG. 1, FIG. 12 illustrates an exemplary remediation subsystem 106, which is shown in FIG. 12 in use with the exemplary fuel dispensing system of FIG. 4. As discussed above and shown in FIG. 4 and also in FIG. 12, the fuel dispensing system includes a storage tank 208, a pipe system 206, and pumps 202. Storage tank 208 is filled with a petroleum product (e.g., gasoline or diesel) through fill line 210, and pumps 202 pump gasoline or diesel from storage tank 206 through pipe system 206 and pumps 202 as needed to fill petroleum tanks of automobiles or trucks.

As shown in FIG. 12, a potential contamination area is covered with a seal 802 that comprises one or more materials that, at least to some degree, seals the ground in and around the potential contamination area. The seal 802 may comprise asphalt and/or concrete disposed on the ground in and around the potential contamination area. The seal 802 may include concrete pedestals to which pumps 202 are attached and paved drive areas that allow automobiles to enter the fuel dispensing station, park next to a pump 202, and then exit the fuel dispensing station.

The potential contamination area (represented generally in FIG. 12 as the area under covering 802) includes an area around the fuel dispensing facility that would likely be contaminated by a discharge of a petroleum product from the fuel dispensing facility (e.g., a discharge of gasoline or diesel from storage tank 208, pipe system 206, and/or pumps 202). The potential contamination area may be determined based on, among other things, the direction and rate of flow of ground water in and around the fuel dispensing facility. The contamination area may also be based on the size of possible discharges from different parts of the fuel dispensing facility.

As shown in FIG. 12, the exemplary remediation subsystem includes injection wells 806 for injecting a cleaning substance (e.g., atmospheric air, a cleaning gas, such as oxygen (which can be in the form of atmospheric oxygen, although pure oxygen can also be injected into wells 806)) into ground water and nutrients into ground soil in and around the potential contamination area (corresponding generally to covering 802). The remediation subsystem also includes extraction wells 808 for extracting air (which may be laden with carbon dioxide) from ground soil in and around the potential contamination area. The remediation subsystem of FIG. 12 also includes one or more compressors 904 (e.g., air vacuum pumps), each connected by pipes 910 to one or more of the injection wells 806. Compressors 904 drive air through pipes 910 to one or more injection wells 806. The remediation subsystem of FIG. 12 further includes one or more air pumps 1002, each connected by pipes 1006 to one or more extraction wells 808. Pumps 1002 draw air out of extraction wells 808. A local wireless master transceiver 1110 provides wireless communications of control, status, and other data to and from compressors 904, air pumps 1002, and/or other elements of the remediation subsystem. Local wireless master transceiver 1110 may communicate using any suitable medium including without limitation radio frequency and infrared transmissions. Rather than using a wireless transceiver master, control and status communications to and/or from compressors 904, air pumps 1002 and other elements of the remediation subsystem of FIG. 12 may be through direct connections (e.g., coaxial cables).

Figure 13:
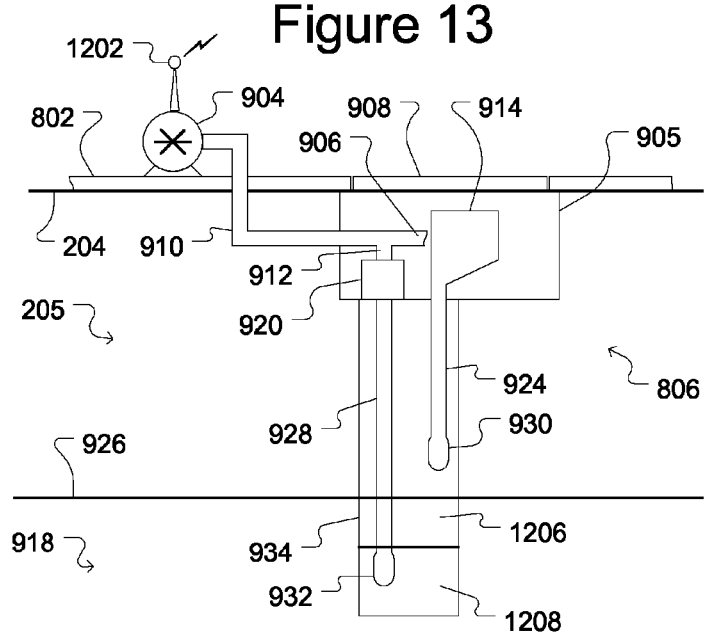
FIG. 13 illustrates a side view of an exemplary injection well (e.g., nutrient and/or air) in the remediation subsystem shown in FIG. 4.

FIG. 13 illustrates an exemplary injection well 806, which is shown in side view. In FIG. 13, line 204 represents ground level (see also FIG. 4), and line 926 represents the water table under the fuel dispensing facility. Area 205 thus represents ground soil (see also FIG. 4) and area 918 represents ground water under the fuel dispensing facility.

As shown in FIG. 13, injection well 806 includes an equipment recess 905 and a bore 934 dug into ground soil 205. Bore 934 may extend into ground water 918 as shown in FIG. 13.

An air conduit (e.g., a plastic, metal, earthen, or non-earthen synthetic pipe) 928 with a perforated end 932 is located in bore 934 and extends into ground water 918. A valve 920 connects air conduit 928 to a branch 912 from piping 910, which is connected to a compressor 904. Piping 910 may extend from 906 to one or more other injection wells 806. Compressor 904 is thus able to drive air through piping 910, valve 920, and air conduit 928 and out perforated end 932 into ground water 918. Sand or gravel 1208 may be deposited around perforated end 932, and a plug (e.g., clay material) 1206 may be deposited on sand or gravel 1208.

As also shown in FIG. 13, a nutrient conduit 924 (e.g., a plastic or metal pipe) with a perforated end 930 is also located in bore 934 and extends into the ground soil 205. Nutrient conduct 924 can alternatively be located in a separate bore (not shown). Nutrients can be deposited (e.g., by a human operator) through opening 914 into nutrient conduit 924. The nutrients can then spread into the ground soil 205 through perforations (e.g., holes, a screen mesh, etc.) in perforated end 930. Sand or gravel (not shown) may be deposited in bore 934 around perforated end 930. Any nutrients that directly or indirectly aide in destroying or neutralizing the type of discharged fuel can be used. For example, nutrients that feed microbes and build protein in the ground soil and ground water, which in turn can aide in destroying or neutralizing the discharged fuel, can be used. Non-limiting examples of such nutrients include ammonium nitrate, ammonium sulfate, ortho phosphate, phosphoric acid, chelated iron, etc.

Compressor 904 may also include a wireless transceiver 1202, which allows control data to be received wirelessly from master transceiver 1110 and status data to be sent wirelessly to master transceiver 1110. Access door 908 through covering 802 provides access to piping 910, valve 920, and nutrient container 914. Opening 914 and nutrient conduit 924 may be refilled as needed manually through access door 908. It should be noted that some injection wells 806 may be constructed without valve 920 and air conduit 928 and some injection wells may be constructed without nutrient container 914 and nutrient conduit 924.

Figure 14:
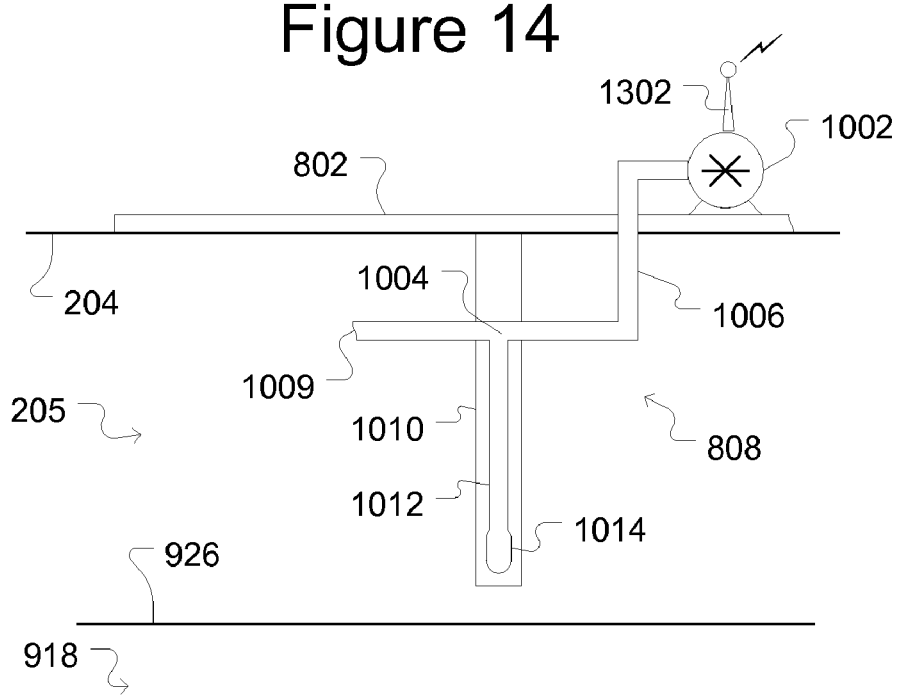
FIG. 14 illustrates a side view of an exemplary gas extraction well in the remediation subsystem shown in FIG. 4.

FIG. 14 illustrates an exemplary extraction well 808, which is shown in side view. Like FIG. 13, line 204 in FIG. 14 represents ground level (see also FIG. 4), and line 926 represents the water table. Area 205 thus represents ground soil and area 918 represents ground water under the fuel dispensing facility.

As shown in FIG. 14, extraction well 1012 includes a bore 1010 into ground soil 205. An extraction conduit 1012 (e.g., a plastic, metal, earthen, or non-earthen synthetic pipe) with a perforated end 1014 is located in bore 1010 and extends into ground soil 205. Sand or gravel (not shown) may be deposited in bore 1010 around perforated end 1014. As also shown, extraction conduit 1012 is connected to a branch 1004 of piping 1006, which is connected to an air pump 1002. Air pump 1002 is thus able to extract air from ground soil 205 through perforated end 1014, extraction conduit 1012, and piping 1006. Piping 1006 may extend from 1009 to extraction conduits in one or more other extraction wells 1012. Air pump 1002 may thus be configured to extract air from multiple extraction wells 808. A shown in FIG. 14, air pump 1002 may include a wireless transceiver 1302, which allows control data to be received wirelessly from master transceiver 1110 and status data to be sent wirelessly to master transceiver 1110 (see FIG. 13).

As discussed in detail in U.S. Pat. No. 6,464,005 (which is incorporated in its entirety herein by reference) and above, the injection of air and nutrients into the ground soil and/or ground water of an area contaminated with a petroleum product (e.g., gasoline, diesel, and/or other fuel remediates), over time, the ground soil and/or ground water. The non-limiting exemplary nutrients discussed above can be used. Covering 802 provides at least some sealing of the surface of the ground 204 and prevents or reduces the amount of surface air drawn into the ground soil by operation of the extraction wells 1012.

Upon determining that the ground soil and/or ground water around the fuel dispensing facility shown in FIG. 12 has become contaminated, for example due to a discharge from the fuel dispensing facility, the exemplary remediation subsystem of FIG. 12 may be operated as follows. Control data may be transmitted from master transceiver 1110 to one or more of compressors 904, turning those compressors 904 on, which, as discussed above, drives air through injection wells 806 into ground soil 205 (see FIG. 13). A human operator may be notified, and the human operator may periodically deposit nutrients through opening 914 into nutrient conduit 924 at one or more injection wells 806. As discussed above, the nutrients will dissipate through perforated end 930 into ground soil 205. The frequency at which nutrients are deposited into nutrient conduit 924, the quantity of nutrients used, and the type of nutrients used depends on the type and/or quantity of contamination. In some embodiments, for petroleum based fuel discharges, nutrients may be deposited once every 1-6 weeks.

Figure 15:
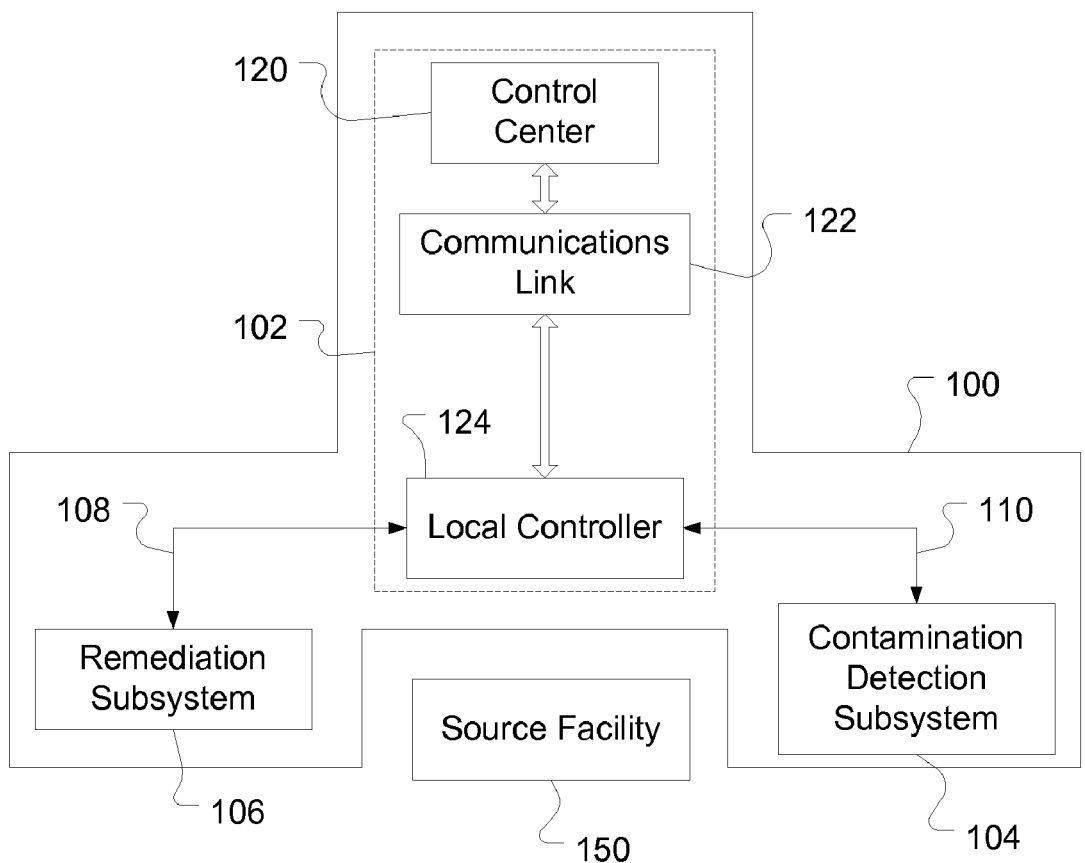
FIG. 15 illustrates the exemplary contamination detection and remediation system of FIG. 4 in which the controller is configured in accordance with the embodiment of the controller shown in FIG. 3.
Figure 16:
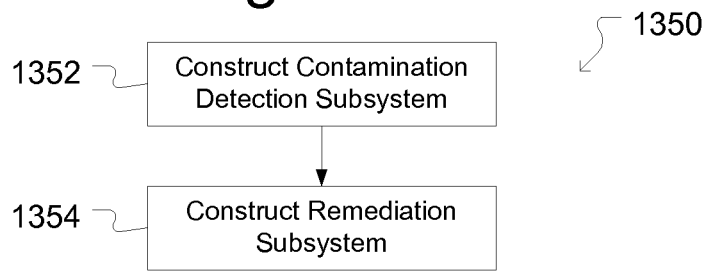
FIG. 16 illustrates an exemplary process for making the contamination detection and remediation system of FIG. 4 according to some embodiments of the invention.

FIG. 15 illustrates an exemplary embodiment of the contamination detection and remediation system 100 of FIG. 1 in which the controller 102 is configured to include a local controller 124, communications link 122, and control center 120 as shown in FIG. 3. FIG. 16 illustrates an exemplary process 1350 for making the contamination detection and remediation system of FIG. 15. As shown in FIG. 16, process 1350 comprises two basic steps: construct a contamination detection subsystem (104 in FIG. 15 and 1352 in FIG. 16), and construct a remediation subsystem (106 in FIG. 15 and 1354 in FIG. 16). Although the invention is not so limited, for ease of discussion and illustration herein, it is assumed that the source facility 150 of FIG. 15 is the fuel dispensing facility shown in FIGS. 4 and 12 (comprising storage tank 208, piping system 206, and pumps 202); the contamination detection subsystem 104 of FIG. 15 is as shown in FIG. 4 (comprising inlet ports 224, 226, 228, 230, 232, intake lines 214, 216, 218, 222, and sensor 212); and the remediation subsystem 106 is as shown in FIG. 12 (comprising injection wells 806, extraction wells 808, and covering 802).

In performing step 1302 of process 1350 of FIG. 16 (to construct the contamination detection subsystem 104 configured as shown in FIG. 4), a gas sensor 212 is selected, and sites where gas is to be sampled from ground soil 205 are selected. Inlet ports 224, 226, 228, 230, 232 are buried at those sites, and intake lines 214, 216, 218, 220 put in place and connected to sensor 212. Communications connection 110 is created by providing communications mechanisms allowing local controller 124 to communicate with sensor 212 and air pump 215.

The sensor 212 should be selected to detect the types of gases present in the fuel stored in storage tank 208 and pumped through pumps 202 and/or the types of gases likely to be produced in ground soil 205 if the fuel is discharged into the ground soil 205. The sensor may be a multi-gas sensor like sensor 400 shown in FIGS. 5A-11 or any other type of sensor capable of detecting the types of gases in ground soil 205 that are indicative of a discharge. Many such sensors are known, and any such sensor may be used. Moreover, sensor 212 may comprise one or more sensors, each configured to detect the presence and approximate concentration of one type of gas that is indicative of a discharge.

Sites where gas is to be sampled from ground soil 205 are preferably located near each element of source facility 150 that could discharge. Inlet ports 224, 226, 228, 230, 232 are then located at those sites. As shown in FIG. 4, inlet ports 224, 226, 228, 230, 232 may be buried in the ground soil 205 near pumps 202, pipe system 206, and storage tank 208, each of which is an element of the exemplary fuel dispensing facility (that is, an exemplary source facility 150) that could discharge fuel. Pipes forming intake lines 214, 216, 218, 220 are buried in ground soil 205 and/or disposed on top of the ground 205, as is convenient, to connect inlet ports 224, 226, 228, 230, 232 to input taps 234, 236, 238, 240 of sensor 212, and an air pump 215 is configured to draw gases out of ground soil 205 through inlet ports 224, 226, 228, 230, 232 through intake lines 214, 216, 218, 220 and into gas sensor 212 as generally shown in FIG. 4. The specific number, locations, and layout of inlet ports 224, 226, 228, 230, 232 and intake lines 214, 216, 218, 220 shown in FIG. 4 is exemplary only. Different numbers, locations, and layouts may be used. Moreover, additional air pumps 215 may be used.

Communications connection 108 is then created to communicatively connect local controller 124 to air pump 215 and sensor 212. (See FIG. 4.) This allows the local controller 124 to send control data to the air pump 215 to turn air pump 215 on and off and set or change operating parameters of air pump 215 (see FIG. 3). Communications connection 110 may also allow local controller 124 to obtain status data from air pump 215. Communications connection 110 also allows local controller 124 to receive data from gas sensor 212 and send control data to gas sensor 212 to turn gas sensor 212 on and off, set operating parameters of gas sensor 212, etc. The communications connection 110 connecting local controller 124 with air pump 215 and sensor 212 may take any convenient form. For example, although not shown in FIG. 4, local controller 124 may include a wireless transceiver like master transceiver 1110 of FIG. 12, and air pump 215 and sensor 212 may include wireless transceivers like 1202 in FIG. 13. In such a configuration, local controller 124 communicates with air pump 215 and sensor 212 wirelessly. Another non-limiting example of communications connection 110 is coaxial cabling between local controller 124, on one hand, and air pump 215 and sensor 212, on the other hand.

Turning now to step 1304 of process 1350 of FIG. 16, constructing a remediation subsystem 106 configured as shown in FIG. 12 involves selecting sites for injection wells 806 and extraction wells 808, constructing injection wells 806 and extraction wells 808, connecting the injection wells 806 to compressors 904 and piping 910, connecting the extraction wells 808 to air pumps 1002 and piping 1006, and providing communications connection 108 by which local controller 124 communicates with compressors 904 and air pumps 1002.

In selecting sites for injection wells 806 and extraction wells 808, those wells are preferably located in and around the potential contamination area discussed above (which generally coincides with the covering 802 shown in FIG. 12). The number, locations, and layout of the injection wells 806 and extraction wells 808 may depend on a number of considerations including without limitation the size of the source facility 150, the type of contaminants that may discharge from source facility 150, etc. As just one example, injection wells 806 may be placed approximately 15 feet from each other in and around the potential contamination area.

Injection wells 806 and extraction wells 808 may be constructed generally as shown in FIGS. 13 and 14. The injection wells 806 and extraction wells 808 may be connected to compressors 904 and air pumps 1002, respectively, by piping 910 and piping 1006 as shown in FIG. 12.

Communications connection 108 is created and configured to communicatively connect local controller 124 to compressors 904 and air pumps 1002. This allows the local controller 124 to send control data to compressors 904 and air pumps 1002 to turn compressors 904 and air pumps 1002 on and off and set or change operating parameters. Communications connection 110 may also allow local controller 124 to obtain status data from compressors 904 and air pumps 1002. The communications connection 108 connecting local controller 124 with compressors 904 and air pumps 1002 may take any convenient form including without limitation wireless transceivers 1110, 916, 1302 of FIGS. 12-14. Another non-limiting example of communications connection 108 is coaxial cabling between local controller 124, on one hand, and compressors 904 and air pumps 1002, on the other hand.

Figure 17:
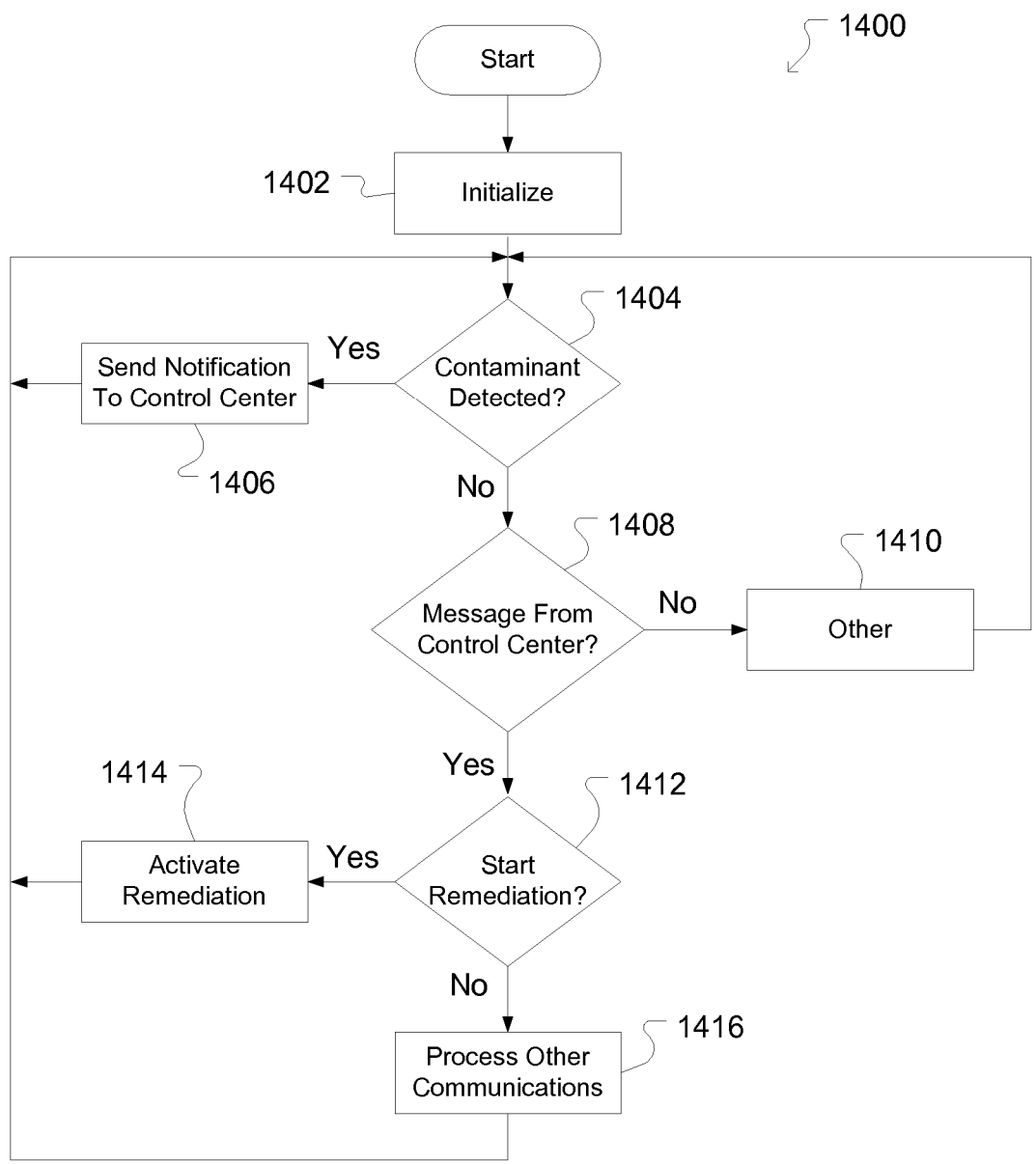
FIG. 17 illustrates exemplary operation of the local controller of the contamination detection and remediation system of FIG. 15 according to some embodiments of the invention.
Figure 18:
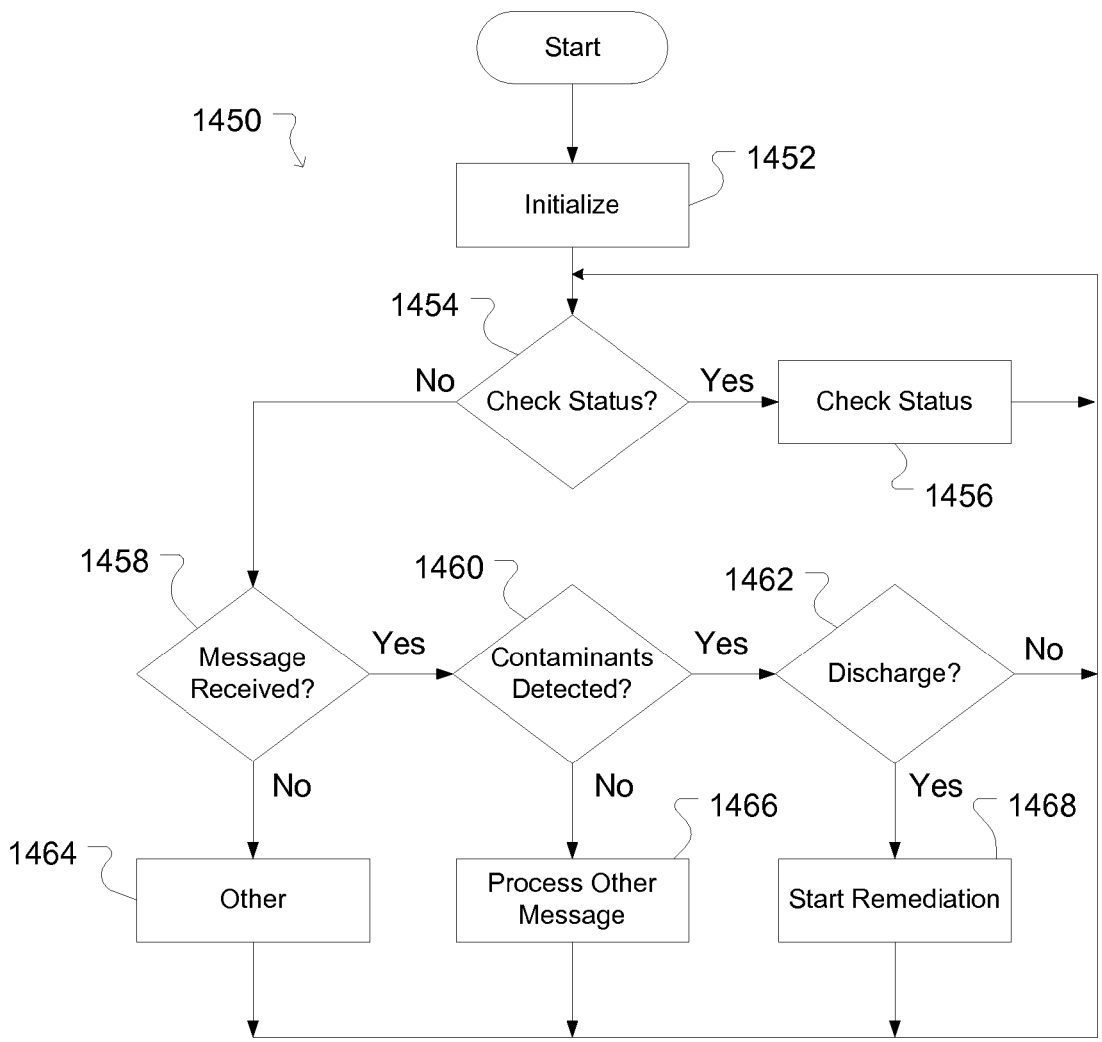
FIG. 18 illustrates exemplary operation of the control center of the contamination detection and remediation system of FIG. 15 according to some embodiments of the invention.

Once contamination detection and remediation system 100 of FIG. 15 is constructed in accordance with process 1350 of FIG. 16, contamination detection and remediation system 100 of FIG. 15 may be operated in accordance with exemplary processes shown in FIGS. 17 and 18. Specifically, process 1400 of FIG. 17 illustrates exemplary operation of local controller 124, and process 1450 of FIG. 18 illustrates exemplary operation of control center 120.

Again, for ease of discussion and illustration, in the discussion of processes 1400 and 1450 that follows, it is assumed that the source facility 150 of FIG. 15 is the fuel dispensing facility shown in FIGS. 4 and 12 (comprising storage tank 208, piping system 206, and pumps 202); the contamination detection subsystem 104 is as shown in FIG. 4 (comprising inlet ports 224, 226, 228, 230, 232, intake lines 214, 216, 218, 222, and sensor 212); and the remediation subsystem 106 is as shown in FIG. 12 (comprising injection wells 806, extraction wells 808, and covering 802).

As shown in FIG. 17, operation of local controller 124 begins with an initialization step 1402 in which local controller 124 initializes contamination detection subsystem 104 and remediation subsystem 106. Initialization 1402 may be performed in response to any of several possible events including without limitation on power up of local controller 124, in response to a command from control center 120, in response to entry of a reset or initialize command received from another source (e.g., a reset switch on local controller 124), etc.

After initialization 1402, local controller 124 executes a loop in which local controller 124 determines whether any of several possible events have occurred. At step 1404, local controller determines whether data received from contamination detection subsystem 104 indicates the possible presence of a contaminant. If so, local controller 124 sends at step 1406 a notification along with applicable data to control center 120. Local controller 124 sends the notification and applicable data via communications link 122.

At step 1408, local controller 124 determines whether a message has been received from control center 120. If so, at step 1412, local controller determines whether the message is a command to active remediation subsystem 106. If so, local controller 124 activates remediation subsystem 106 at step 1414. Local controller 124 may do so by sending control signals to compressors 904 and air pumps 808 turning compressors 904 and air pumps 808 on. Alternatively, the message may command local controller 124 to start only a portion of remediation subsystem 106 at step 1414. Although not shown in FIG. 17, the progress of the remediation of the discharge can be monitored by monitoring the concentrations of oxygen ($O_2$), carbon dioxide ($CO_2$), and/or hydrocarbons ($C_1$-$C_{35+}$). For example, the remediation subsystem 106 can be operated until the concentrations of carbon dioxide ($CO_2$) and/or hydrocarbons ($C_{12[1]}$-$C_{35+}$, hydrocarbons, methane, etc.) detected in the ground soil 205 fall to acceptable levels (e.g., concentrations that would not be indicative of contamination of ground soil 205 with a petroleum product such as gasoline and/or diesel). Alternatively or in addition, concentrations of oxygen ($O_2$) in ground soil 205 can be monitored (e.g., using sensor 400 of FIGS. 5A-11), and the remediation subsystem 106 can be operated until concentrations of oxygen ($O_2$) in ground soil 205 indicate that the discharged petroleum product has been sufficiently remediated. As one non-limiting example, the following concentrations of oxygen ($O_2$) in ground soil into which the petroleum product was discharged may indicate sufficient remediation of the ground soil: at least about 10%, at least about 15%, or at least about 20%. In some applications, a concentration of oxygen at or near at least 20.9% can indicate sufficient remediation.

Many other types of messages may be received from control center 120. Identification of any other such messages and execution of any commands associated with such messages are represented generically in process 1400 by step 1416 in which such other messages (and associated commands) are processed. Non-limiting examples of such other messages include a command to turn on or off contamination detection subsystem 104; a command to turn off remediation subsystem 106; a command to change operating settings and/or parameters of contamination detection subsystem 104 and/or remediation subsystem 106; a request for status relating to local controller 124, contamination detection subsystem 104, and/or remediation subsystem 106; etc.

Returning to step 1408, if local controller 124 determines that a message has not been received from control center 120, local controller may perform any number of other functions represented generically as "other" at step 1410. In addition, although not shown in FIG. 17, provisions for terminating process 1400 and handling errors may also be included.

Process 1400 of FIG. 17 may be implemented in whole or in part as software running on a computer or processor at local controller 124. For example, as discussed above with respect to FIG. 3, local controller 124 may comprise one or more computers operating under software control. Alternatively, local controller 124 may comprise a processor and memory like those shown in FIG. 2. Rather than being implemented in software, the process 1400 of FIG. 17 may alternatively be implemented in hardwired logic circuits or in a combination of software and hardwired logic circuits. As yet another alternative, a human operator may perform some or all of the process 1400.

Turning now to FIG. 18, operation of control center 120 also begins with initialization at step 1452, which may include initializing control center 120 and/or sending messages to local controller 124 that cause initialization of local controller 124, contamination detection subsystem 104, and/or remediation subsystem 106.

At step 1454, control center 120 determines whether to check the status of local controller 124, contamination detection subsystem 104, and/or remediation subsystem 106. If so, control center 120 sends at step 1456 a message to local controller 124 requesting status (which may be one of the miscellaneous messages processed at step 1416 in FIG. 17).

Control center 120 may store data scheduling times for periodic status checks of local controller 124, contamination detection subsystem 104, and/or remediation subsystem 106.

At step 1458, control center 120 determines whether control center 120 has received a message. If so, control center 120 determines at step 1460 whether the message indicates possible detection of contaminants at source facility 150. (For example, as discussed above, local controller 124 may send such a message at step 1406 of FIG. 17.) If the message indicates possible detection of contaminants at step 1460, control center 120 determines at step 1462 whether a discharge has likely occurred at source facility 150. Control center 120 may do so in any number of different ways. For example, the message received from local controller 124 may include data identifying detected gases and indicating concentrations of those gases in the ground soil 205 under or around source facility 150. In performing step 1462, control center 120 may analyze the data to determine whether the detected gases and the concentrations indicate a likely discharge at source facility 150. As one non-limiting example, a more than negligible change in levels of hydrocarbons in ground soil around a gasoline dispensing station can indicate a possible discharge of a petroleum product (e.g., gasoline or diesel fuel) into surrounding ground soil. In some applications, a change of at least about 5-10 times the level of hydrocarbons in the ground soil can indicate a possible discharge of the petroleum product into surrounding ground soil. For example, a change from 100 parts-per-million hydrocarbons to 1000 parts-per-million can indicate a discharge of gasoline or diesel fuel.

If control center 120 determines at step 1462 that a discharge has likely occurred, control center 120 starts a remediation process at step 1468. Control center 120 may do so by sending one or more messages to local controller 124 with commands to start all or part of remediation subsystem 106. (As discussed above, such a message is identified and executed by local controller 124 at steps 1412, 1414 of FIG. 17.)

Returning to step 1458, if control center 120 determined at step 1458 that a message was received but then determines at step 1460 that the message was not a message indicating possible contamination, control center 1466 identifies the message and takes any actions associated with the message at step 1466. Any number of possible messages may be received by control center 120.

If control center 120 determines at step 1458 that a message has not been received, control center 120 may perform any number of other functions represented generically as "other" at step 1464. In addition, although not shown in FIG. 18, provisions for terminating process 1450 and handling errors may also be included.

Process 1450 of FIG. 18 may be implemented in whole or in part as software running on a computer or processor at control center 120. For example, as discussed above with respect to FIG. 3, control center 120 may comprise one or more computers operating under software control. Alternatively, control center 120 may comprise a processor and memory like those shown in FIG. 2. Rather than being implemented in software, the process 1450 of FIG. 18 could alternatively be implemented in hardwired logic circuits or in a combination of software and hardwired logic circuits. As yet another alternative, some or all of the steps of process 1450 may be performed by a human at control center 120. Indeed, process 1450 may be implemented in part in software running on a computer at control center 120, and the software may prompt a human operator for input and/or to take actions in which the operator performs some of the functions or steps in process 1450.

Figure 19:
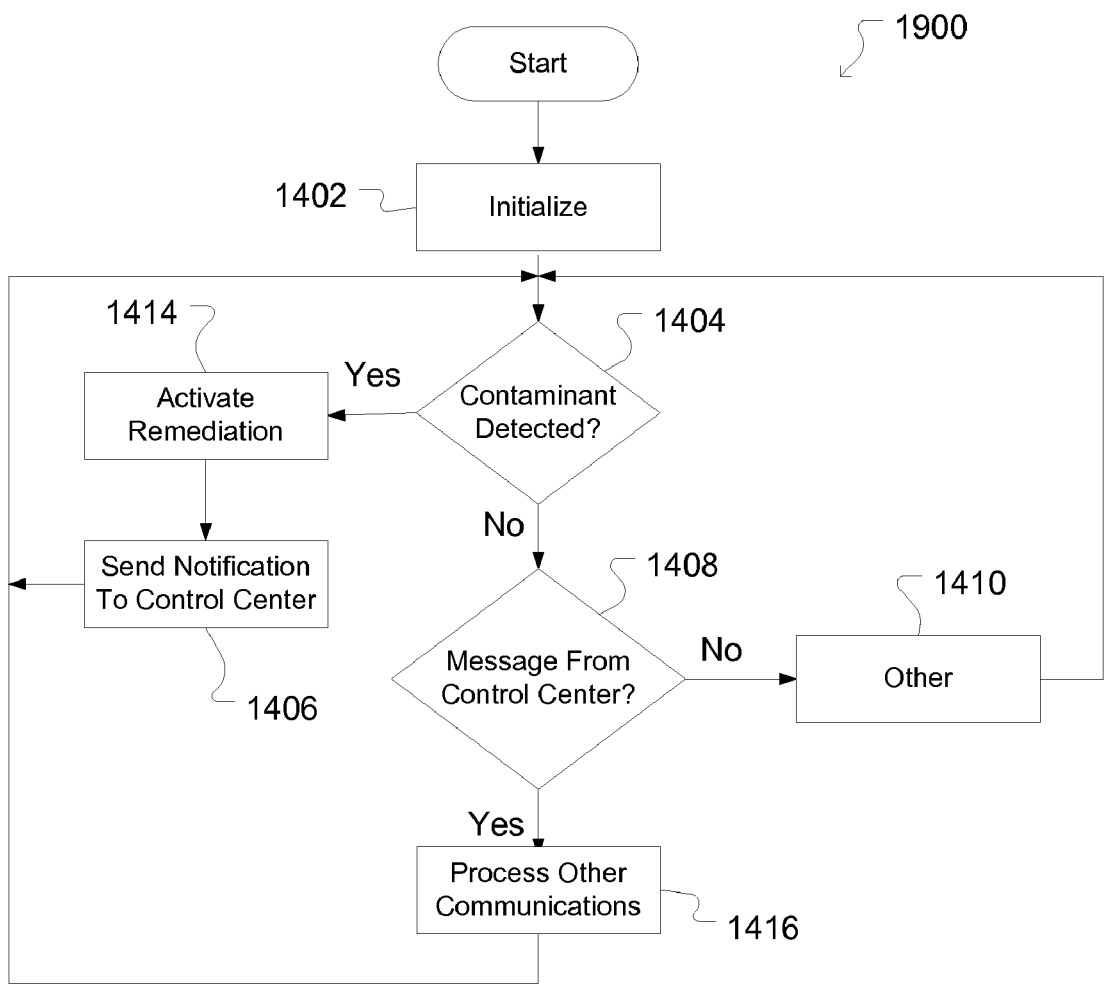
FIG. 19 illustrates another exemplary operation of the local controller of the contamination detection and remediation system of FIG. 15.

The processes shown in FIGS. 17 and 18 are exemplary only and many modifications are possible. For example, in FIG. 17, upon detecting the presence of a contaminant at step 1404, the process 1400 can be modified to activate remediation (as in step 1414) rather than or in addition to sending a notification to the control center at step 1406. FIG. 19 illustrates an example of such a modified process 1900. As shown, in FIG. 19, steps 1402, 1404, 1406, 1408, 1410, 1414, and 1416 can be generally the same as similarly numbered steps in the process 1400 shown in FIG. 17. In FIG. 19, however, upon detecting a contaminant at step 1404, the local controller 124 activates the remediation subsystem at step 1414 and sends a notification at step 1406 as shown in FIG. 19.

Figure 20:
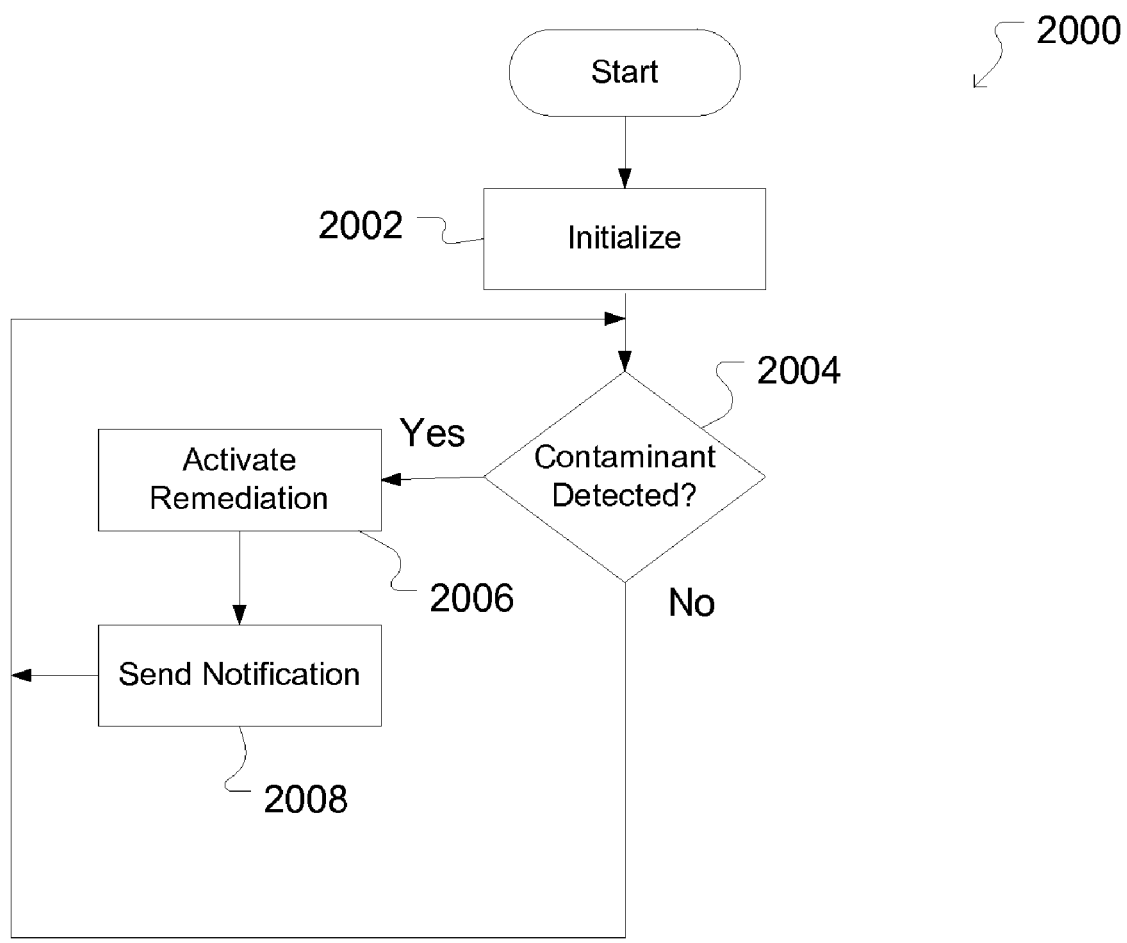
FIG. 20 illustrates exemplary operation of the exemplary configuration shown in FIG. 2 of the controller of FIG. 1.

FIG. 20 illustrates an exemplary process 200 that can be performed by processor 110 of the exemplary configuration of controller 102 shown in FIG. 2, which as discussed above, can be located entirely at the site of the source facility 150 (see FIG. 1). As shown, at step 2002, the processor 110 can initialize the contamination detection subsystem 104 and the remediation subsystem 106. At step 2004, the processor 110 can determine whether a contaminant is detected, and if so, at step 2006, the processor 110 can activate the remediation subsystem 106 (see FIG. 1), and optionally, send a notification at step 2008. The notification sent at step 2008 can be in any form. For example, notification can be sent in the form of a coded telephone message to the operators of the source facility 150. As another example, notification can be sent in the form of an email notification generated by the processor 110.

Figure 21:
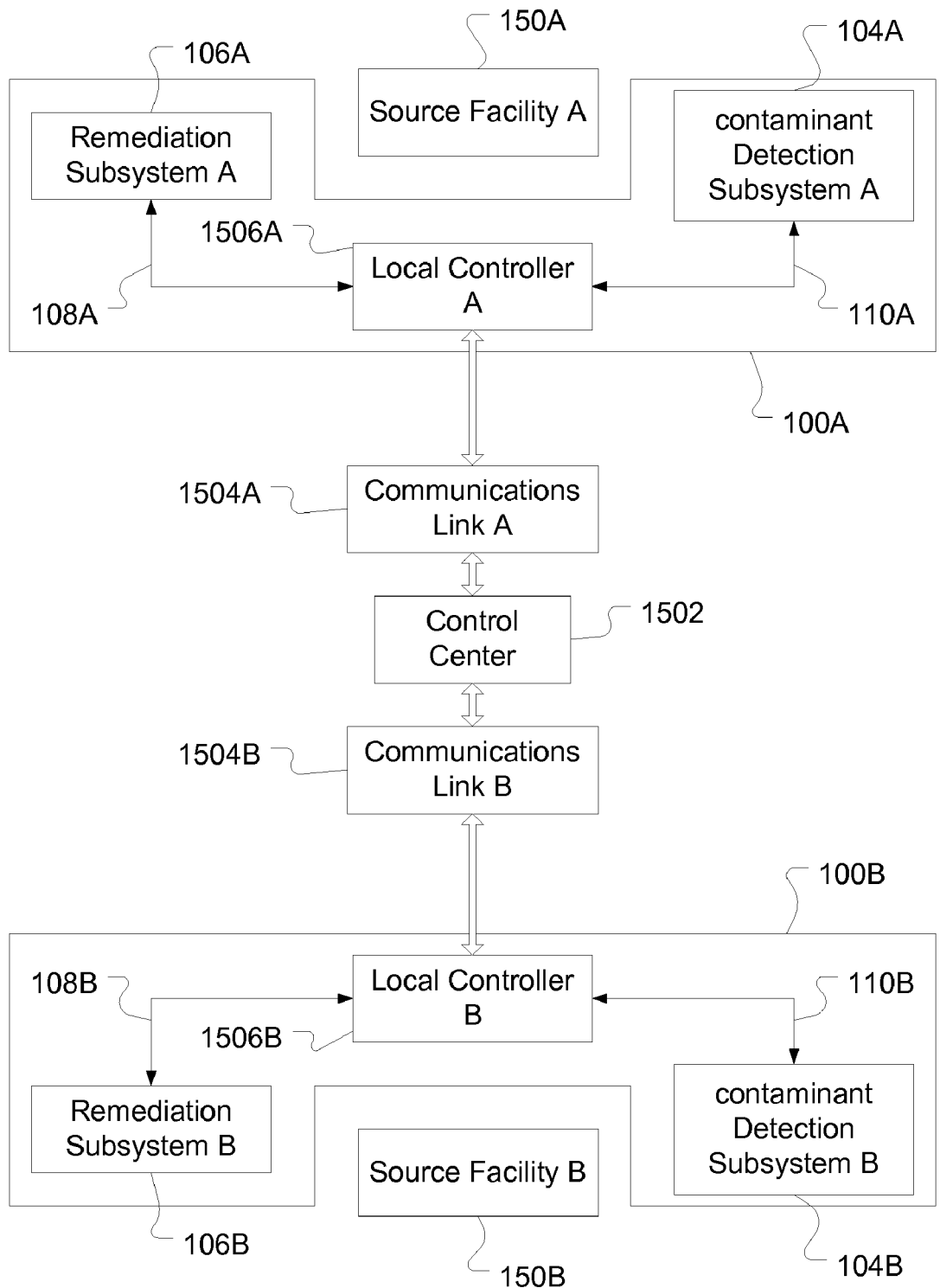
FIG. 21 illustrates a control center configured to monitor and control contamination detection and remediation at multiple source facilities according to some embodiments of the invention.

FIG. 21 illustrates an exemplary configuration in which a control center 1502 is configured to monitor and control multiple local controllers 1506A and 1506B, remediation subsystems 106A and 106B, and contamination detection subsystems 104A and 104B at multiple source facilities 150A and 150B. In the example shown in FIG. 21, control center 1502 communicates with a local controller A 1506A through a communications link A 1504A. Local controller A 1506A controls contamination detection subsystem A 104A and remediation subsystem A 106A, which are located near source facility A 150A and configured to detect and remediate, respectively, discharges at source facility A 150A. Communications connections 108A, 110A provide communications between local controller A 1506A and remediation subsystem 106A and contamination detection subsystem A 104A, respectively. Likewise, local Controller B 1506B controls contamination detection subsystem B 104B and contaminant detection subsystem B 104B, which are located near source facility B 150B and configured to detect and remediate, respectively, discharges at source facility B 150B. Communications connections 108B, 110B provide communications between local controller B 1506B and remediation subsystem 106B and contamination detection subsystem B 104B, respectively.

Control center 1502 may operate generally like control center 120 except that control center 1502 is configured to control a plurality of contamination detection and remediation systems 100A, 100B. (Although two contamination detection and remediation systems 100A, 100B are shown in FIG. 21, control center 1502 may be configured to control more than two contamination detection and remediation systems 100A, 100B.) Communications link A 1504A and communication link B 1504B may be similar to and operate like communications link 122 of FIGS. 3 and 12. Similarly, local controller A 1506A and local controller B 1506B may be similar to and operate like local controller 124 of FIGS. 3 and 15. Remediation subsystem A 106A and remediation subsystem B 106B, contamination detection subsystem A 104A and contamination detection subsystem B 104B, and communications connections 108A, 110A, 108B, 110B may be similar to and operate like similarly named elements in FIGS. 3 and 15.

Figure 22:
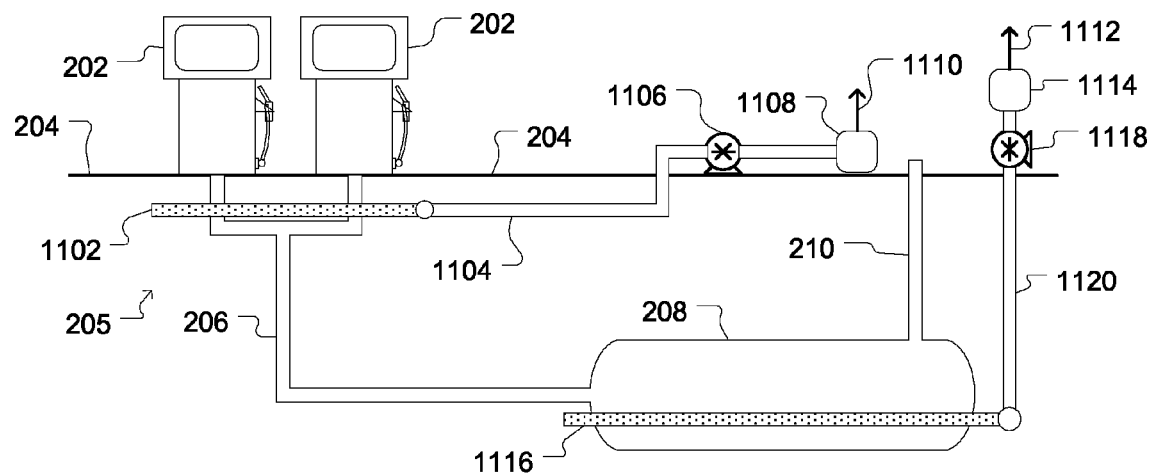
FIG. 22 illustrates a side view and FIG. 23 illustrates a top view of another configuration of the contamination detection system of FIG. 1 deployed with the exemplary source facility shown in FIG. 4 according to some embodiments of the invention.
Figure 23:
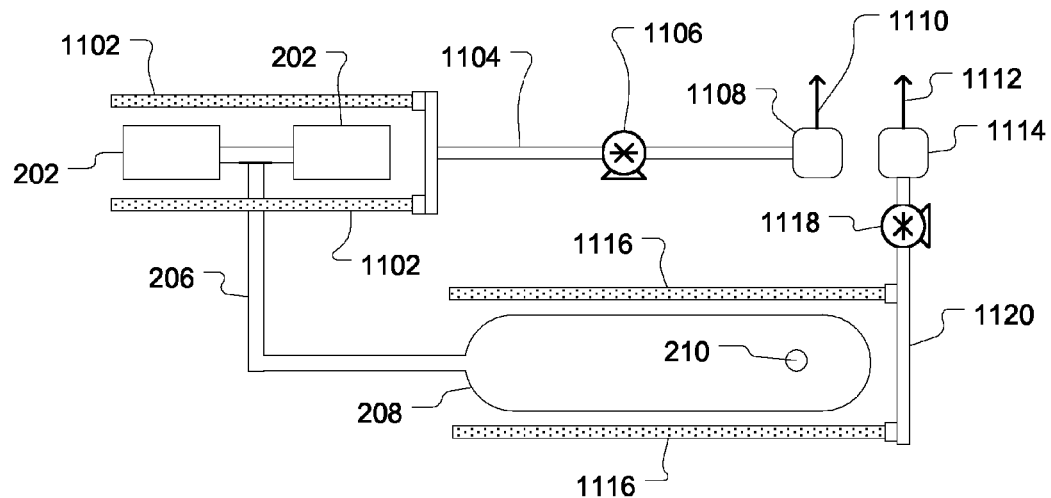

FIG. 22 illustrates a side view and FIG. 23 a top view of another exemplary configuration of a contamination detection subsystem that can be used in detection and remediation system 100 of FIG. 1 as contamination detection subsystem 104, according to some embodiments of the invention. As shown in FIGS. 22 and 23, the contamination detection subsystem shown in FIGS. 22 and 23 is illustrated as deployed with a source facility like source facility 150 of FIG. 1 comprising pumps 202, pipe system 206, storage tank 208, and fill like 210.

As shown in FIGS. 22 and 23, the illustrated contamination detection subsystem comprises inlet pipes 1102 disposed near pumps 202. Inlet pipes 1102—which include holes or perforations along all or part of their lengths—are connected by intake line 1104 to a sensor 1108. A compressor 1106 draws air and vapors from ground soil 205 through the holes or perforations in inlet pipes 1102 into sensor 1108. The contamination detection subsystem shown in FIGS. 22 and 23 can also comprise inlet pipes 1116 disposed near storage tank 208. Inlet pipes 1116 can be generally similar to inlet pipes 1102 (e.g., having holes or perforations along all or part of their lengths) and can be connected to sensor 1114 through inlet line 1120.

Sensors 1108 and 1114 can be configured like sensor 212 of FIG. 4 (which, as discussed above, can be like the exemplary sensor 400 shown in FIGS. 5A-1). Sensor 1108 can output one or more signals 1110, and sensor 1114 can output one or more signals 1112. For example, signals 1110, 1112 can be output to a controller like controller 102 of FIG. 1, local controller 124 of FIG. 15, or one of local controller A 1506A or local controller B 1506B of FIG. 21.

Signal(s) 1110 can indicate, among other things, the, presence, identity, and/or concentrations of one or more gases detected by sensor 1108 in the gases and vapors drawn from ground soil 205 through inlet pipe 1102. Signal(s) 1112 output by sensor 1114 can be similar to signal(s) 1110 output by sensor 1108. In the configuration of contamination detection subsystem shown in FIGS. 22 and 23, signals 1110, 1112 can also indicate the location of detected gases or vapors and thus indicate the likely source of a fuel discharge into ground soil 205. For example, the detection at sensor 1108 of a gas or vapor indicative of diesel fuel is necessarily detected in the vicinity of pumps 202 (because inlet pipes 1102 are disposed near pumps 202) and therefore suggests that pumps 202 may have discharged diesel fuel into ground soil 205. Similarly, detection at sensor 1114 of gas or vapor indicative of diesel fuel suggests that storage tank 208 may be discharging diesel fuel.

In the exemplary configuration of contamination detection subsystem shown in FIGS. 22 and 23, the source facility is thus divided into areas or regions (e.g., a region around pumps 202 and a region around storage tank 208) and a separate sensor 1108, 1114 is supplied with gas and vapors sampled from the ground soil 205 in each region. The location of gases or vapors indicating a discharge of fuel from the source facility can thus be isolated to a particular region and the source of the discharge identified as a portion of the source facility located in that region. Although two such regions are shown in FIGS. 22 and 23 (one region around pumps 202 and one region around storage tank 208), more or fewer regions can be implemented. Moreover, a remediation system (e.g., like 106 of FIG. 1 or any remediation system disclosed herein) can also be divided into similar regions such that only the portion of the remediation system where a discharge is detected is activated.

The configurations shown in FIGS. 22 and 23 are exemplary only, and many modifications are possible. For example, one compressor (e.g., like compressor 1106 or 1118 can draw air through intake line 1104 and inlet line 1102). As another example, intake line 1104 and inlet line 1120 can feed one sensor (e.g., like sensor 1108 or 1114).

Although specific embodiments and applications of the invention have been described in this specification, there is no intention that the invention be limited to these exemplary embodiments and applications or to the manner in which the exemplary embodiments and applications operate or are described herein. For example, although all of the embodiments and examples discussed above involved a discharge of contaminants, principles of the invention may be used to monitor a facility or site where a predetermined level of contaminants may be knowingly or even purposely discharged into the surrounding environment. In such an application, the invention may be configured to detect levels of the contaminants that exceed a predetermined acceptable level and trigger remediation.

We claim:

1. A system for detecting and remediating a discharge of fuel from a fuel source facility, said system comprising:
    a contamination detection subsystem comprising sensor means for: (1) sampling gases or vapors from ground soil adjacent said fuel source facility, and (2) detecting a presence in said sampled gases or vapors of any of a plurality of contaminate gases or vapors indicative of a discharge of said fuel from said fuel source facility into said ground soil;
    a remediation subsystem comprising remediation means for remediating contamination in said ground soil due to said discharge of fuel from said fuel facility into said ground soil; and
    a controller connected to said contamination detection subsystem and said remediation subsystem by electronic data communication connections, said controller comprising electronic control means for: (1) monitoring electronic data output by said sensor means, (2) determining whether said electronic data indicates said discharge of said fuel into said ground soil, and (3) if said electronic data indicates said discharge of said fuel into said ground soil, automatically turning on at least a portion of said remediation subsystem by providing electronic control data to said remediation subsystem and thereby causing said at least a portion of said remediation subsystem to start remediating contamination in said ground soil due to said discharge of fuel.

2. The system of claim 1, wherein said contaminate gases or vapors include vapors from diesel fuel.

3. The system of claim 1, wherein said contaminate gases or vapors include methane.

4. The system of claim 1, wherein said contamination detection subsystem further comprises extracting means for extracting gases or vapors from said ground soil and providing said extracted gases or vapors to said sensor means.

5. The system of claim 4, wherein said extracting means comprises one or more perforated pipes and an air vacuum pump.

6. The system of claim 4, wherein said extracting means is further for continuously extracting vapors from said ground soil and providing said extracted vapors to said sensor means.

7. The system of claim 4, wherein:
said contaminate gases or vapors include hydrocarbons, and
said electronic control means is further for determining whether said electronic data indicates an increase in a level of at least one of said hydrocarbons in said sampled gases or vapor, wherein said electronic control means determines that said electronic data indicates said discharge of said fuel into said ground soil if said electronic data indicates said increase in said level of said at least one of said hydrocarbons in said sampled gases or vapor.

8. The system of claim 7, wherein said hydrocarbons include hydrocarbons $C_1$ to $C_{35+}$.

9. The system of claim 7, wherein said hydrocarbons include hydrocarbons $C_{12}$ to $C_{35}$.

10. The system of claim 7, wherein said increase is an increase of at least five times the level of said at least one of said hydrocarbons.

11. The system of claim 1, wherein said remediation subsystem comprises injecting means for injecting a cleaning substance into an area contaminated by said discharge of fuel.

12. The system of claim 11, wherein said injecting means injects said cleaning substance into ground water in a vicinity of said fuel source facility.

13. The system of claim 11, wherein said cleaning substance comprises atmospheric air.

14. The system of claim 11, wherein said remediation subsystem further comprises extracting means for extracting air from said ground soil.

15. The system of claim 14, wherein said at least a portion of said remediation subsystem automatically turned on by said control means comprises said extracting means.

16. The system of claim 11, wherein said at least a portion of said remediation subsystem automatically turned on by said control means comprises said injecting means.

17. The system of claim 1, wherein said contamination detection subsystem further comprises extraction wells configured to extract vapors from said ground soil, and said extraction wells are disposed in said ground soil below a seal that at least partially seals at least part of said ground soil.

18. The system of claim 1, wherein said electronic control means is further for continuously (1) monitoring said electronic data output by said sensor means, (2) determining whether said electronic data indicates said discharge of said fuel into said ground soil, and (3) if said electronic data indicates said discharge of said fuel into said ground soil, automatically turning on said at least a portion of said remediation subsystem by providing electronic control data to said remediation subsystem and thereby causing said at least a portion of said remediation subsystem to start remediating contamination in said ground soil due to said discharge of fuel.

19. The system of claim 1, wherein said electronic control means comprises a digital memory and a digital processor communicatively connected to said digital memory.

20. The system of claim 1, wherein said control means is further for, if said electronic data indicates said discharge of said fuel into said ground soil, automatically communicating over an electronic communications system to a remote location a message that said discharge of said fuel was detected.

21. The system of claim 1, wherein said sensor means comprises:
a chamber;
a material comprising a chemical reactant disposed within said chamber;
a beam generator disposed outside of said chamber and configured to direct a plurality of energy beams through said chamber, each of said energy beams having a different wavelength in a different wavelength range that is absorbed by a different one of said contaminate gases;
a first detector disposed outside said chamber and positioned to receive said energy beams, said first detector configured to generate signals proportional to an energy level of each of said energy beams; and
a second detector disposed outside said chamber and positioned to detect and generate an output signal proportional to an output energy generated by a chemical reaction in said chamber of another one of said contaminate gases in said chamber with said chemical reactant, wherein said another one of said contaminate gases does not absorb energy from any of said plurality of energy beams,
wherein said electronic data output by said sensor means comprises said signals generated by said first detector and said second detector.

* * * * *